(12) United States Patent
Pennell et al.

(10) Patent No.: US 9,101,100 B1
(45) Date of Patent: Aug. 11, 2015

(54) METHODS AND MATERIALS FOR HIGH THROUGHPUT TESTING OF TRANSGENE COMBINATIONS

(71) Applicant: Ceres, Inc., Thousand Oaks, CA (US)

(72) Inventors: Roger I. Pennell, Malibu, CA (US); Richard Hamilton, Calabasas, CA (US); Michael F. Portereiko, Thousand Oaks, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 14/327,217

(22) Filed: Jul. 9, 2014

Related U.S. Application Data

(60) Provisional application No. 61/986,705, filed on Apr. 30, 2014.

(51) Int. Cl.
*A01H 1/04* (2006.01)
*C12Q 1/68* (2006.01)
*C12N 15/82* (2006.01)

(52) U.S. Cl.
CPC .............. *A01H 1/04* (2013.01); *C12N 15/8209* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 4,987,071 A | 1/1991 | Cech et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,254,678 A | 10/1993 | Haseloff et al. |
| 5,538,880 A | 7/1996 | Lundquist et al. |
| 6,013,863 A | 1/2000 | Lundquist et al. |
| 6,127,606 A | 10/2000 | Bennett et al. |
| 6,172,279 B1 | 1/2001 | Bridges et al. |
| 6,255,558 B1 | 7/2001 | Haseloff et al. |
| 6,326,527 B1 | 12/2001 | Kirihara et al. |
| 6,329,571 B1 | 12/2001 | Hiei |
| 6,399,857 B1 | 6/2002 | Kloti |
| 6,423,885 B1 | 7/2002 | Waterhouse et al. |
| PP13,008 P2 | 9/2002 | Walsh |
| 6,452,067 B1 | 9/2002 | Bedbrook et al. |
| 6,573,099 B2 | 6/2003 | Graham |
| 6,706,470 B2 | 3/2004 | Choo et al. |
| PP14,743 P2 | 5/2004 | Speichert et al. |
| 6,753,139 B1 | 6/2004 | Baulcombe et al. |
| 6,777,588 B2 | 8/2004 | Waterhouse et al. |
| PP15,193 P2 | 9/2004 | Smith et al. |
| 6,946,586 B1 | 9/2005 | Fromm et al. |
| PP16,176 P3 | 1/2006 | Cosner et al. |
| 7,166,767 B2 | 1/2007 | da Costa e Silva et al. |
| 7,173,121 B2 | 2/2007 | Fang |
| 7,179,904 B2 | 2/2007 | Kwok |
| 7,193,129 B2 | 3/2007 | Reuber et al. |
| 7,196,245 B2 | 3/2007 | Jiang et al. |
| 7,214,789 B2 | 5/2007 | Pennell |
| 7,223,904 B2 | 5/2007 | Heard et al. |
| 7,244,879 B2 | 7/2007 | Christensen et al. |
| 7,262,054 B2 | 8/2007 | Jamieson et al. |
| 7,273,923 B2 | 9/2007 | Jamieson et al. |
| PP18,161 P2 | 10/2007 | Probst |
| 7,312,376 B2 | 12/2007 | Apuya et al. |
| 7,378,571 B2 | 5/2008 | Apuya |
| 7,402,667 B2 | 7/2008 | Cook et al. |
| 7,429,692 B2 | 9/2008 | Dang |
| 7,476,777 B2 | 1/2009 | Mascia |
| 7,485,775 B2 | 2/2009 | da Costa e Silva et al. |
| 7,502,113 B2 | 3/2009 | Deppermann et al. |
| 7,521,597 B2 | 4/2009 | da Costa e Silva et al. |
| 7,598,367 B2 | 10/2009 | Cook et al. |
| 7,803,983 B2 | 9/2010 | Alexandrov et al. |
| 7,838,650 B2 | 11/2010 | Pennell et al. |
| 7,851,608 B2 | 12/2010 | Cook et al. |
| 7,939,328 B1 | 5/2011 | Saito et al. |
| 8,022,273 B2 | 9/2011 | Christensen et al. |
| 8,034,915 B2 | 10/2011 | Haseloff et al. |
| 8,049,068 B2 | 11/2011 | Nazdan et al. |
| 8,076,535 B2 | 12/2011 | Jankowski et al. |
| 8,222,482 B2 | 7/2012 | Bobzin et al. |
| 8,278,434 B2 | 10/2012 | Cook et al. |
| 8,299,320 B2 | 10/2012 | Schneeberger et al. |
| 8,324,454 B2 | 12/2012 | Zhou et al. |
| 8,344,210 B2 | 1/2013 | Kwok et al. |
| 8,362,322 B2 | 1/2013 | Apuya et al. |
| 8,389,805 B2 | 3/2013 | Apuya et al. |
| 8,471,099 B2 | 6/2013 | Schneeberger et al. |

(Continued)

FOREIGN PATENT DOCUMENTS

| | | |
|---|---|---|
| WO | WO 97/01952 | 1/1997 |
| WO | WO 97/30164 | 8/1997 |

(Continued)

OTHER PUBLICATIONS

Liu et al. Advanced genetic tools for plant biotechnology. 2013. Nature Reviews Genetics. 14:781-793.*
Naqvi et al. When more is better: multigene engineering in plants. 2010. Trends Plant Sci. 15(1):48-56.*
Lu et al._Plant Physiol_146_1482_2008.*
U.S. Appl. No. 60/505,689, filed Sep. 23, 2003, Cook et al.
U.S. Appl. No. 60/518,075, filed Nov. 6, 2003, Pennell et al.
U.S. Appl. No. 60/544,771, filed Feb. 13, 2004, Cook et al.

(Continued)

*Primary Examiner* — Medina A Ibrahim
*Assistant Examiner* — Russell Boggs
(74) *Attorney, Agent, or Firm* — Fish & Richardson P.C.

(57) ABSTRACT

High throughput methods are described for identifying combinations of transgenes that can be used to improve a phenotypic feature in an organism. Large populations of organisms (e.g., plants) containing different combinations of transgenes as well as different promoter-coding sequence combinations can be assessed using the methods.

26 Claims, 2 Drawing Sheets

(56) References Cited

U.S. PATENT DOCUMENTS

| | | |
|---|---|---|
| 8,481,814 B2 | 7/2013 | Feldmann |
| 8,728,808 B2 | 5/2014 | Dhadialla et al. |
| 2003/0175783 A1 | 9/2003 | Waterhouse et al. |
| 2003/0175965 A1 | 9/2003 | Lowe et al. |
| 2003/0180945 A1 | 9/2003 | Wang et al. |
| 2004/0214330 A1 | 10/2004 | Waterhouse et al. |
| 2005/0032221 A1 | 2/2005 | Chang et al. |
| 2006/0015970 A1 | 1/2006 | Pennell et al. |
| 2006/0021083 A1 | 1/2006 | Cook et al. |
| 2006/0041952 A1 | 2/2006 | Cook |
| 2006/0041961 A1 | 2/2006 | Abad et al. |
| 2006/0075522 A1 | 4/2006 | Cleveland et al. |
| 2006/0260004 A1 | 11/2006 | Fang et al. |
| 2006/0265788 A1 | 11/2006 | Rommens |
| 2007/0006335 A1 | 1/2007 | Cook et al. |
| 2007/0056058 A1 | 3/2007 | Olivier et al. |
| 2007/0056688 A1 | 3/2007 | Kim et al. |
| 2007/0136839 A1 | 6/2007 | Cook et al. |
| 2007/0294782 A1 | 12/2007 | Abad et al. |
| 2008/0050820 A1 | 2/2008 | Shirley |
| 2008/0148432 A1 | 6/2008 | Abad |
| 2008/0235823 A1 | 9/2008 | Medrano et al. |
| 2008/0295196 A1 | 11/2008 | Abad et al. |
| 2008/0301839 A1 | 12/2008 | Ravanello |
| 2009/0031438 A1 | 1/2009 | Kennard et al. |
| 2009/0031451 A1 | 1/2009 | da Costa e Silva et al. |
| 2009/0044288 A1 | 2/2009 | Abad et al. |
| 2009/0070897 A1 | 3/2009 | Goldman et al. |
| 2009/0100536 A1 | 4/2009 | Adams et al. |
| 2009/0106866 A1 | 4/2009 | Lu et al. |
| 2009/0144847 A1 | 6/2009 | Shaikh et al. |
| 2009/0144849 A1 | 6/2009 | Lutfiyya |
| 2009/0172840 A1 | 7/2009 | Wang et al. |
| 2009/0181851 A1 | 7/2009 | Cook et al. |
| 2009/0293154 A1 | 11/2009 | Yelin et al. |
| 2009/0304901 A1 | 12/2009 | Bobzin et al. |
| 2010/0015407 A1 | 1/2010 | Be et al. |
| 2010/0017904 A1 | 1/2010 | Abad et al. |
| 2010/0024070 A1 | 1/2010 | Bobzin et al. |
| 2010/0037346 A1 | 2/2010 | Cook et al. |
| 2010/0269222 A1 | 10/2010 | Medrano et al. |
| 2011/0016587 A1 | 1/2011 | Cook et al. |
| 2011/0041219 A1 | 2/2011 | Cook et al. |
| 2011/0061122 A1 | 3/2011 | Christensen et al. |
| 2011/0061124 A1 | 3/2011 | Nadzan et al. |
| 2011/0119791 A1 | 5/2011 | Ronen et al. |
| 2011/0126323 A1 | 5/2011 | Karchi et al. |
| 2011/0179529 A1 | 7/2011 | Kwok et al. |
| 2011/0197315 A1 | 8/2011 | Emmanuel et al. |
| 2011/0265199 A1 | 10/2011 | Zhou |
| 2011/0283378 A1 | 11/2011 | Mascia et al. |
| 2012/0060234 A1 | 3/2012 | Emmanuel et al. |
| 2012/0297505 A1 | 11/2012 | Wu et al. |
| 2013/0014292 A1 | 1/2013 | Pennell et al. |
| 2013/0117881 A1 | 5/2013 | Cook et al. |
| 2013/0125263 A1 | 5/2013 | Apuya et al. |
| 2013/0174298 A1 | 7/2013 | Christensen et al. |
| 2013/0191943 A1 | 7/2013 | Apuya |
| 2014/0007286 A1 | 1/2014 | Ghislain |
| 2014/0059714 A1 | 2/2014 | Matarasso et al. |

FOREIGN PATENT DOCUMENTS

| | | |
|---|---|---|
| WO | WO 98/36083 | 8/1998 |
| WO | WO 98/53083 | 11/1998 |
| WO | WO 99/32619 | 7/1999 |
| WO | WO 02/46449 | 6/2002 |
| WO | WO 2005/098007 | 10/2005 |
| WO | WO 2006/005023 | 1/2006 |
| WO | WO 2006/034479 | 3/2006 |
| WO | WO 2006/036864 | 4/2006 |
| WO | WO 2006/045829 | 5/2006 |
| WO | WO 2006/066193 | 6/2006 |
| WO | WO 2007/011681 | 1/2007 |
| WO | WO 2007/044988 | 4/2007 |
| WO | WO 2007/055826 | 5/2007 |
| WO | WO 2007/064724 | 6/2007 |
| WO | WO 2007/120989 | 10/2007 |
| WO | WO 2007/127501 | 11/2007 |
| WO | WO 2007/144190 | 12/2007 |
| WO | WO 2008/062049 | 5/2008 |
| WO | WO 2008/092910 | 8/2008 |
| WO | WO 2009/009142 | 1/2009 |
| WO | WO 2009/099899 | 8/2009 |
| WO | WO 2009/146015 | 12/2009 |
| WO | WO 2010/039750 | 4/2010 |
| WO | WO 2010/075143 | 7/2010 |

OTHER PUBLICATIONS

U.S. Appl. No. 60/558,869, filed Apr. 1, 2004, Cook et al.
U.S. Appl. No. 60/583,609, filed Jun. 30, 2004, Alexandrov.
U.S. Appl. No. 60/583,691, filed Jun. 30, 2004, Alexandrov et al.
U.S. Appl. No. 60/612,891, filed Sep. 23, 2004, Kwok.
U.S. Appl. No. 60/637,140, filed Dec. 16, 2004, Feldmann.
U.S. Appl. No. 60/757,544, filed Jan. 9, 2006, Dang.
U.S. Appl. No. 60/776,307, filed Feb. 24, 2006, Kwok.
Abler and Scandalios, "Isolation and characterization of a genomic sequence encoding the maize Cat3 catalase gene," Plant Mol. Biol., 1993, 22:10131-1038.
Akashi et al., "Gene Discovery by Ribozyme and siRNA Libraries," Nature Rev Mol. Cell Biol, 2005, 6:413-422.
Anand et al., "Development of a Lesion-Mimic Phenotype in a Transgenic Wheat Line Overexpressing Genes for Pathogenesis-Related (PR) Proteins is Dependent on Salicylic Acid Concentration," MPMI, 2003, 16(10):916-925.
Anderson and Hanson, "The Arabidopsis Mei2 homologue AML1 binds AtRaptor1B, the plant homologue of a major regulator of eukaryotic cell growth," BMC Plant Biol., 2005, 5:2, 8 pages.
Baerson et al., "Developmental regulation of an acyl carrier protein promoter in vegetative and reproductive tissues," Plant Mol.. Biol., 1993, 22(2):255-267.
Braga et al., "Expression of the Cry1Ab Protein in Genetically Modified Sugarcane for the Control of Diatraea saccharalis (Lepidoptera: Crambidae)," J New Seeds, 2003, 5:209-221.
Bustos and Schleif, "Functional domains of the AraC protein," PNAS, 1993, 90(12):5638-42.
Bustos et al., "Regulation of β-Glucuronidase Expression in Transgenic Tobacco Plants by an A/T-Rich, cis-Acting Sequence Found Upstream of a French Bean β-Phaseolin Gene," Plant Cell, 1989, 1(9):839-853.
Cai et al., "Targeted transgene integration in plant cells using designed zinc finger nucleases," Plant Mol Biol., 2009 69(6):699-709.
Cerdan et al., "A 146 bp fragment of the tobacco Lhcb1*2 promoter confers very-low-fluence, low-fluence and high-irradiance responses of phytochrome to a minimal CaMV 35S promoter," Plant Mol. Biol., 1997, 33:245-255.
Chen et al., "Functional analysis of regulatory elements in a plant embryo-specific gene," Proc. Natl. Acad. Sci. USA, 1986, 83:8560-8564.
Conceicao and Krebbers, "A cotyledon regulatory region is responsible for the different spatial expression patterns of Arabidopsis 2S albumin genes," Plant, 1994, 5:493-505.
Conkling et al., "Isolation of Transcriptionally Regulated Root-Specific Genes from Tobacco," Plant Physiol., 1990, 93:1203-1211.
Dai et al., "RF2b, a rice bZIP transcription activator, interacts with RF2a and is involved in symptom development of rice tungro disease," Proc. Natl. Acad. Sci. USA, 2004, 101(2):687-692.
Day et al., "Transgene integration into the same chromosome location can produce alleles that express at a predictable level, or alleles that are differentially silenced," Genes Dev., 2000, 14:2869-2880.
de Feyter and Gaudron, "Expressing Ribozymes in Plants," Methods in Molecular Biology, 1997, 74(43):403-415.
Fejes et al., "A 268 bp upstream sequence mediates the circadian clock-regulated transcription of the wheat Cab-1 gene in transgenic plants," Plant Mol. Biol., 1990, 15:921-932.

(56) References Cited

OTHER PUBLICATIONS

Fromm et al., "An Octopine Synthase Enhancer Element Directs Tissue-Specific Expression and Binds ASF-1, a Factor from Tobacco Nuclear Extracts," Plant Cell, 1989, 1:977-984.
GenBank No. AF096096, 1999, 2 pages.
GenBank No. AF129516, 1999, 2 pages.
GenBank No. L05934, 1993, 3 pages.
GenBank No. U93215, 2002, 42 pages.
Goff et al., "Identification of functional domains in the maize transcriptional activator C1: comparison of wild-type and dominant inhibitor proteins," Gene Dev., 1991, 5:298-309.
Greaves and O'Hare, "Separation of requirements for protein-DNA complex assembly from those for functional activity in the herpes simplex virus regulatory protein Vmw65," J. Virol., 1989, 63:1641-1650.
Green et al., "Binding site requirements for pea nuclear protein factor GT-1 correlate with sequences required for light-dependent transcriptional activation of the rbcS-3A gene," EMBO J., 1988, 7:4035-4044.
Hellauer et al., "A novel DNA binding motif for yeast zinc cluster proteins: the Leu3p and Pdr3p transcriptional activators recognize everted repeats," Mol. Cell. Biol., 1996, 16:6096-6102.
Hong et al., "Promoter sequences for two different Brassica napus tapetal oleosin-like genes direct tapetal expression of β-glucuronidase in transgenic Brassica plants," Plant Mol. Biol., 1997, 34(3):549-555.
Jordano et al., "A Sunflower Helianthinin Gene Upstream Sequence Ensemble Contains an Enhancer and Sites of Nuclear Protein Interaction," Plant Cell, 1989, 1:855-866.
Kasuga et al., "Improving plant drought, salt and freezing tolerance by gene transfer of a single stress-inducible transcription factor," Nature Biotech, 1999, 17:287-291.
Keller et al., "Vascular-Specific Expression of the Bean GRP 1.8 Gene is Negatively Regulated," Plant Cell, 1991, 3(10):1051-1061.
Krizek and Sulli, "Mapping sequences required for nuclear localization and the transcriptional activation function of the Arabidopsis protein Aintegumenta," Planta, 2006, 224(3):612-21.
Lam et al., "Site-specific mutations alter in vitro factor binding and change promoter expression pattern in transgenic plants," Proc. Natl. Acad. Sci. USA, 1989, 86:7890-7894.
Li et al., "Site-Specific Integration of Transgenes in Soybean via Recombinase-Mediated DNA Cassette Exchange," Plant Physiol., Nov. 2009, 151:1087-1095.
Lloyd et al., "Targeted mutagenesis using zinc-finger nucleases in Arabidopsis," Proc. Natl. Acad. Sci. USA, 2005, 102:2232-2237.
Luan et al., "A Rice cab Gene Promoter Contains Separate cis-Acting Elements that regulate expression in Dicot and Monocot Plants," Plant Cell, 1992, 4:971-981.
Lubberstedt et al., "Promoters from Genes for Plastid Proteins Possess Regions with Different Sensitivities toward Red and Blue Light," Plant Physiol., 1994, 104:997-1006.
Maas, "The arginine repressor of *Escherichia coli*," Microbiol Review, 1994, 58:631-640.
Mamane et al., "A linker region of the yeast zinc cluster protein leu3p specifies binding to everted repeat DNA," J Biol Chem., 1998, 273(29):18556-61.
Mansfield and Mumm, "Survey of Plant Density Tolerance in U.S. Maize Germplasm," Crop Science, 2014, 57:157-173.
Matsuoka et al., "Tissue-specific light-regulated expression directed by the promoter of a C4 gene, maize pyruvate, orthophosphate dikinase, in a C3 plant, rice," Proc. Natl. Acad. Sci. USA, 1993, 90:9586-9590.
Matzke et al., "RNAi-Mediated Pathways in the Nucleus," Nature Reviews Genetics, 2005, 6:24-35.
McCarty et al., "The Viviparous-1 Development Gene of Maize Encodes a Novel Transcriptional Activator," Cell, 1991, 66:895-905.
Medberry et al., "The Commelina Yellow Mottle Virus Promoter is a Strong Promoter in Vascular and Reproductive Tissues," Plant Cell, 1992, 4(2):185-192.

Meier et al., "Elicitor-Inducible and Constitutive in Vivo DNA Footprints Indicate Novel cis-Acting Elements in the Promoter of a Parsley Gene encoding Pathogenesis-Related Protein 1," Plant Cell, 1991, 3:309-316.
Mittal, "Improving the efficiency of RNA interference in mammals," Nature Reviews Genetics, 2004, 5:355-365.
Moore et al., "A transcription activation system for regulated gene expression in transgenic plants," PNAS, Jan. 1998, 95(1):376-81.
Okanami et al., "HALF-1, a bZIP-type protein, interacting with the wheat transcription factor HBP-1a contains a novel transcriptional activation domain," Genes Cells, 1996, 1(1):87-99.
Onodera et al., "A rice functional transcriptional activator, RISBZ1, responsible for endosperm-specific expression of storage protein genes through GCN4 motif," J. Biol. Chem., 2001, 276(17):14139-52.
Perriman et al., "Effective ribozyme delivery in plant cells," Proc. Natl. Acad. Sci. USA, 1995, 92(13):6175-6179.
Petolino et al., "Zinc finger nuclease-mediated transgene deletion," Plant Mol Biol., 2010, 73(6):617-628.
Richards et al., "Construction of a GFP-BAR plasmid and its use for switchgrass transformation," Plant Cell. Rep., 2001, 20:48-54.
Riggs et al., "Cotyledone Nuclear Proteins Bind to DNA Fragments Harboring Regulatory Elements of Phytohemagglutinin Genes," Plant Cell, 1989, 1(6):609-621.
Samis et al., "Pyramiding Mn-Superoxide dismutase transgenes to improve persistence and biomass production in alfalfa," J Exp Botany, May 2002, 53(372):1343-1350.
Sheridan et al., "The mac1 Gene: Controlling the Commitment to the Meiotic Pathway in Maize," Genetics, 1996, 142:1009-1020.
Shukla et al., "Precise genome modification in the crop species *Zea mays* using zinc-finger nucleases," Nature, 2009, 459:437-441.
Slocombe et al., "Temporal and Tissue-Specific Regulation of a Brassica napus Stearoyl-Acyl Carrier Protein Desaturase Gene," Plant Physiol., 1994, 104(4):167-176.
Somleva et al., "Agrobacterium-Mediated Genetic Transforamtion of Switchgrass," Crop Sci., 2002, 42:2080-2087.
Tovkach et al., "A Toolbox and procedural notes for characterizing novel zinc finger nucleases for genome editing in plant cells," Plant J, 2009, 57:747-757.
Townsend et al., "High-frequency modification of plant genes using engineered zinc-finger nucleases," Nature, 2009, 459:442-445.
Truernit et al., "The promoter of the Arabidopsis thaliana SUC2 sucrose-H+ symporter gene directs expression of β-glucuronidase to the phloem: Evidence for phloem: loading and unloading by SUC2," Planta, 1995, 196:564-570.
Urao et al., "Molecular cloning and characterization of a gene that encodes a MYC-related protein in Arabidopsis," Plant Mol. Biol., 1996, 32:571-57.
Van Eenenaam et al., "Elevation of seed alpha-tocopherol levels using plant-based transcription factors targeted to an endogenous locus," Metab Eng., 2004, 6(2):101-8.
Wade et al., "Genomic analysis of LexA binding reveals the permissive nature of the *Escherichia coli* genome and identifies unconventional target sites," Genes Dev., 2005, 19:2619-2630.
Xie and Yang, "RNA-guided genome editing in plants using a CRISPR-Cas system," Mol. Plant, 2013, 6:1975-1983.
Yamamoto et al., "The Promoter of a Pine Photosynthetic Gene Allows Expression of a β-Glucuronidase Reporter Gene in Transgenic Rice Plants in a Light-Independent but Tissue-Specific Manner," Plant Cell Physiol., 1994, 35:773-778.
Yan et al., "New Construct Approaches for Efficient Gene Silencing in Plants," Plant Physiol., 2006, 141: 1508-1518.
Yanagisawaa and Sheen, "Involvement of maize Dof zinc finger proteins in tissue-specific and light-regulated gene expression," Plant Cell, 1998, 10(1):75-89.
Zhang et al., "DNA Sequences that Activate Isocitrate Lyase Gene Expression during Late Embryogenesis and during Postgerminative Growth," Plant Physiology, 1996, 110:1069-1079.
Zhang et al., "Transcription activator-like effector nucleases enable efficient plant genome engineering," Plant Physiology 2013, 161:20-27.

(56) References Cited

OTHER PUBLICATIONS

Zheng et al., "SPK1 is an Essential S-Phase-Specific Gene of *Saccharomyces cerevisiae* that Encodes a Nuclear Serin/Threonine/Tyrosine Kinase," Mol. Cell Biol., 1993, 13:5829-5842.

Zhu et al., "The C Terminus of AvrXa10 Can Be Replaced by the Transcriptional Activation Domain of VP16 from the Herpes Simplex Virus," Plant Cell, 1999, 11:1665-1674.

* cited by examiner

A – Direct Fusion Construct

B – Two component system

SEQUENCE LISTING

```
<160> NUMBER OF SEQ ID NOS: 11

<210> SEQ ID NO 1
<211> LENGTH: 10
<212> TYPE: DNA
<213> ORGANISM: Artificial Sequence
<220> FEATURE:
<223> OTHER INFORMATION: UAS from LEU3 of S. cerevisiae
<220> FEATURE:
<221> NAME/KEY: misc_feature
<222> LOCATION: 4, 5, 6, 7
<223> OTHER INFORMATION: n = A,T,C or G

<400> SEQUENCE: 1 ccgnnnncgg                                                           10

<210> SEQ ID NO 2
<211> LENGTH: 17
<212> TYPE: DNA
<213> ORGANISM: Artificial Sequence
<220> FEATURE:
<223> OTHER INFORMATION: UAS of GAL4 of S. cerevisiae
<220> FEATURE:
<221> NAME/KEY: misc_feature
<222> LOCATION: 4, 5, 6, 7, 8, 9, 10, 11, 12, 13, 14
<223> OTHER INFORMATION: n = A,T,C or G

<400> SEQUENCE: 2
cggnnnnnnn nnnnccg                                                   17

<210> SEQ ID NO 3
<211> LENGTH: 20
<212> TYPE: DNA
<213> ORGANISM: Artificial Sequence
<220> FEATURE:
<223> OTHER INFORMATION: UAS of HAP1 of S. cerevisiae

<400> SEQUENCE: 3
agcacggact tatcggtcgg                                                20

<210> SEQ ID NO 4
<211> LENGTH: 22
<212> TYPE: DNA
<213> ORGANISM: Artificial Sequence
<220> FEATURE:
<223> OTHER INFORMATION: exemplary HAP1 UAS

<400> SEQUENCE: 4
gcagcggtat taacgggatt ac                                             22

<210> SEQ ID NO 5
<211> LENGTH: 12
<212> TYPE: DNA
<213> ORGANISM: Artificial Sequence
<220> FEATURE:
<223> OTHER INFORMATION: UAS of PPR1 of S. cerevisiae
<220> FEATURE:
<221> NAME/KEY: misc_feature
<222> LOCATION: 4, 5, 6, 7, 8, 9
```

```
<223> OTHER INFORMATION: n = A,T,C or G

<400> SEQUENCE: 5
cggnnnnnnc cg                                                              12

<210> SEQ ID NO 6
<211> LENGTH: 20
<212> TYPE: DNA
<213> ORGANISM: Artificial Sequence
<220> FEATURE:
<223> OTHER INFORMATION: exemplary PPR1 UAS

<400> SEQUENCE: 6
tcttcggcaa ttgccgaaga                                                      20

<210> SEQ ID NO 7
<211> LENGTH: 19
<212> TYPE: DNA
<213> ORGANISM: Artificial Sequence
<220> FEATURE:
<223> OTHER INFORMATION: exemplary LEU3p UAS

<400> SEQUENCE: 7
cctgcgggta ccggcttgg                                                       19

<210> SEQ ID NO 8
<211> LENGTH: 20
<212> TYPE: DNA
<213> ORGANISM: Artificial Sequence
<220> FEATURE:
<223> OTHER INFORMATION: UAS of LexA of Escherichia coli

<400> SEQUENCE: 8
aattgtgagc gctcacaatt                                                      20

<210> SEQ ID NO 9
<211> LENGTH: 20
<212> TYPE: DNA
<213> ORGANISM: Artificial Sequence
<220> FEATURE:
<223> OTHER INFORMATION: UAS of Lac operon of Escherichia coli

<400> SEQUENCE: 9
aattgtgagc gctcacaatt                                                      20

<210> SEQ ID NO 10
<211> LENGTH: 18
<212> TYPE: DNA
<213> ORGANISM: Artificial Sequence
<220> FEATURE:
<223> OTHER INFORMATION: UAS of ArgR of Escherichia coli
<220> FEATURE:
<221> NAME/KEY: misc_feature
<222> LOCATION: 2, 17
<223> OTHER INFORMATION: n = A,T,C or G

<400> SEQUENCE: 10
wntgaatwww wattcanw                                                        18

<210> SEQ ID NO 11
<211> LENGTH: 17
<212> TYPE: DNA
<213> ORGANISM: Artificial Sequence
```

```
<220> FEATURE:
<223> OTHER INFORMATION: UAS of AraC of Escherichia coli

<400> SEQUENCE: 11
tatggataaa aatgcta                                                    17
```

METHODS AND MATERIALS FOR HIGH THROUGHPUT TESTING OF TRANSGENE COMBINATIONS

CROSS-REFERENCE TO RELATED APPLICATIONS

This application claims priority from U.S. Provisional Application Ser. No. 61/986,705, filed on Apr. 30, 2014, which is incorporated herein by reference in its entirety.

TECHNICAL FIELD

This document relates to methods and materials for improving one or more phenotypic features in an organism. For example, this document provides high throughput methods for identifying combinations of transgenes that improve one or more phenotypic features in an organism (e.g., a plant).

BACKGROUND

The first generation of transgenic plant products has been successful because the transgenes are conferring traits, such as glyphosate herbicide tolerance and insect resistance, that make transgenic plants markedly different. Development of the second generation of transgenic traits has met with limited success despite significant efforts in the field. Similarly to plant breeding efforts, the second generation transgenic traits are often aimed at incrementally improving agronomic performance or product quality. For these transgenic phenotypes, high-level overexpression is often undesirable, so identification of potential transgene expressed sequences is followed by a search for their optimal promoters. Moreover, single transgenes often have substantial impact in specific germplasm or environmental conditions, but significantly diminished impact when tested in a different genetic background or environment. Traditionally, transgenes are evaluated in replicated plots, where field performance and phenotypes of plants with a transgene or stack of transgenes (i.e., a combination of transgenes) is carefully compared to that of nearby controls. This approach requires significant effort in phenotyping.

SUMMARY

This document provides methods and materials for improving one or more phenotypic features in an organism. For example, this document provides high throughput methods for identifying combinations of transgenes that can be used to improve a phenotypic feature in an organism. As described herein, large populations of organisms (e.g., plants) containing different combinations of target transgenes as well as different promoter-coding sequence combinations can be grown side-by-side. These large populations of organisms are genetically nearly identical, except for the specific transgene combinations in each plant. The particular combinations that result in desirable phenotypes can be identified based on improved quality or performance in the field or greenhouse or lab testing. Expressing combinations of transgenes can generate significant phenotypes as their transgenic effects may be additive or synergistic.

In one aspect, this document features a method for identifying a combination of genetic elements that improves a phenotype of a plant. The method includes (a) selecting at least four target transgenes (e.g., 4, 5, 6, 7, 8, 9, 10, 11, 12, 13, 14, 15, or more target transgenes), wherein each target transgene of the at least four target transgenes comprises an upstream activating sequence followed by a nucleotide sequence to be expressed; (b) selecting at least two activator transgenes (e.g., 2, 3, 4, 5, 6, 7, 8, 9, 10, 11, 12, 13, 14, 15, or more activator transgenes), wherein each activator transgene comprises a plant promoter operably linked to a sequence encoding a polypeptide comprising a DNA binding domain fused to a transcription activation domain, wherein each DNA binding domain of the at least two activator transgenes binds to at least one upstream activating sequence of the at least four target transgenes; (c) obtaining a first parental plant and a second parental plant, wherein each of the at least four target transgenes and the at least two activator transgenes is individually present in either the first parental plant or the second parental plant, is unlinked from each of the other of the at least four target transgenes and the at least two activator transgenes that are present within the same first parental plant or second parental plant, and is in a hemizygous state within the first parental plant or the second parental plant; (d) sexually crossing the first parental plant and the second parental plant to produce a population of progeny plants; (e) selecting at least one progeny plant the population as having an improved phenotype to obtain a selected progeny plant, and (f) determining which target transgenes and activator transgenes are present within the selected progeny plant, thereby identifying a combination of genetic elements that improves a phenotype of a plant. The method can include repeating steps (a) through (f), wherein the selecting of step (a) and the selecting of step (b) comprises the target transgenes and the activator transgenes determined to be present within the selected progeny plant in step (f). The selecting of step (e) can be based at least in part on performance under field testing conditions. The selecting of step (e) can be based at least in part on water use efficiency, nitrogen use efficiency, or plant density stress performance under field testing conditions. The nucleotide sequence to be expressed can be a nucleotide sequence encoding a polypeptide. The first and second parental plants can be isogenic. The first parental plant can include at least four target transgenes, and the second parental plant can include at least two activator transgenes. The polypeptide encoded by each of the at least two activator transgenes can be the same. The upstream activating sequence of each of the at least four target transgenes can be the same. The plant promoter of each of the at least two activator transgenes can be different. The first parental plant and the second parental plant can be selected from the group consisting of *Zea mays, Sorghum bicolor*, and *Oryza sativa*. The first parental plant or the second parental plant can be cytoplasmically male sterile. The first parental plant and the second parental plant can belong to distinct heterotic groups.

This document also features a method for making a collection of seeds. The method can include (a) selecting at least four target transgenes (e.g., 4, 5, 6, 7, 8, 9, 10, 11, 12, 13, 14, 15, or more target transgenes), wherein each target transgene of the at least four target transgenes comprises an upstream activating sequence followed by a nucleotide sequence to be expressed; (b) selecting at least two activator transgenes (e.g., 2, 3, 4, 5, 6, 7, 8, 9, 10, 11, 12, 13, 14, 15, or more activator transgenes), wherein each activator transgene comprises a plant promoter operably linked to a sequence encoding a polypeptide comprising a DNA binding domain fused to a transcription activation domain, wherein each DNA binding domain of the at least two activator transgenes binds to at least one upstream activating sequence of the at least four target transgenes; (c) obtaining a first parental plant and a second parental plant, wherein each of the at least four target transgenes and the at least two activator transgenes is individually present in either the first parental plant or the second parental plant, is unlinked from each of the other of the at least four target transgenes and the at least two activator transgenes that are present within the same first parental plant or second parental plant, and is in a hemizygous state within the first parental plant or the second parental plant; (d) sexually crossing the first parental plant and the second parental plant to produce a population of progeny plants; (e) selecting at least one progeny plant from the population as having an improved phenotype to obtain a selected progeny plant; (f) determining which target transgenes and activator transgenes are present within the selected progeny plant, thereby identifying a combination of genetic elements that improves a phenotype of a plant, and (g) making a collection of seeds, wherein the cells of the seeds comprise the combination of genetic elements. The method can include repeating steps (a) through (f), wherein the selecting of step (a) and the selecting of step (b) comprises the target transgenes and the activator transgenes determined to be present within the selected progeny plant in step (f). The selecting of step (e) can be based at least in part on performance under field testing conditions. The selecting of step (e) can be based at least in part on water use efficiency, nitrogen use efficiency, or plant density stress performance under field testing conditions. The nucleotide sequence to be expressed can be a nucleotide sequence encoding a polypeptide. The first and second parental plants can be isogenic. The first parental plant can include at least four target transgenes, and the second parental plant can include at least two activator transgenes. The polypeptide encoded by each of the at least two activator transgenes can be the same. The upstream activating sequence of each of the at least four target transgenes can be the same. The plant promoter of each of the at least two activator transgenes can be different. The first parental plant and the second parental plant can be selected from the group consisting of *Zea mays, Sorghum bicolor*, and *Oryza sativa*. The first parental plant or the second parental plant can be cytoplasmically male sterile. The first parental plant and the second parental plant can belong to distinct heterotic groups.

This document also features a method for making a plant. The method includes (a) selecting at least four target transgenes (e.g., 4, 5, 6, 7, 8, 9, 10, 11, 12, 13, 14, 15, or more target transgenes), wherein each target transgene of the at least four target transgenes comprises an upstream activating sequence followed by a nucleotide sequence to be expressed; (b) selecting at least two activator transgenes (e.g., 2, 3, 4, 5, 6, 7, 8, 9, 10, 11, 12, 13, 14, 15, or more activator transgenes), wherein each activator transgene comprises a plant promoter operably linked to a sequence encoding a polypeptide comprising a DNA binding domain fused to a transcription activation domain, wherein each DNA binding domain of the at least two activator transgenes binds to at least one upstream activating sequence of the at least four target transgenes; (c) obtaining a first parental plant and a second parental plant, wherein each of the at least four target transgenes and the at least two activator transgenes is individually present in either the first parental plant or the second parental plant, is unlinked from each of the other of the at least four target transgenes and the at least two activator transgenes that are present within the same first parental plant or second parental plant, and is in a hemizygous state within the first parental plant or the second parental plant; (d) sexually crossing the first parental plant and the second parental plant to produce a population of progeny plants; (e) selecting at least one progeny plant from the population as having an improved phenotype to obtain a selected progeny plant; (f) determining which target transgenes and activator transgenes are present within the selected progeny plant, thereby identifying a combination of genetic elements that improves a phenotype of a plant, and (g) making a plant, wherein the cells of the plant comprise the combination of genetic elements. The method can include repeating steps (a) through (f), wherein the selecting of step (a) and the selecting of step (b) comprises the target transgenes and the activator transgenes determined to be present within the selected progeny plant in step (f). The selecting of step (e) can be based at least in part on performance under field testing conditions. The selecting of step (e) can be based at least in part on water use efficiency, nitrogen use efficiency, or plant density stress performance under field testing conditions. The nucleotide sequence to be expressed can be a nucleotide sequence encoding a polypeptide. The first and second parental plants can be isogenic. The first parental plant can include at least four target transgenes, and the second parental plant can include at least two activator transgenes. The polypeptide encoded by each of the at least two activator transgenes can be the same. The upstream activating sequence of each of the at least four target transgenes can be the same. The plant promoter of each of the at least two activator transgenes can be different. The first parental plant and the second parental plant can be selected from the group consisting of *Zea mays, Sorghum bicolor*, and *Oryza sativa*. The first parental plant or the second parental plant can be cytoplasmically male sterile. The first parental plant and the second parental plant can belong to distinct heterotic groups.

In one aspect, this document features a method of identifying a combination of transgenes that improves a phenotypic feature of an organism. The method includes obtaining a first and a second parental organism, at least one of the first or the second parental organism comprising a plurality of unlinked hemizygous transgenes, wherein the gametes of at least one of the first or the second parental organisms contain independently segregating subgroups of the plurality of transgenes; sexually crossing the first and second parental organisms to produce a progeny population having different combinations of the plurality of transgenes; and identifying the combination of transgenes that improves the phenotypic feature in the progeny population. The first and second parental organisms can be the same organism. The first parental organism can include the plurality of unlinked hemizygous transgenes and the second parental organism can be a non-transgenic organism. Such a method also can be used to produce a collection of seeds, e.g., by identifying a combination of transgenes using the method; obtaining a first parental plant, wherein the first parental plant is isogenic and the first parental plant comprises a plurality of target transgenes (e.g., four or more target transgenes, such as 4, 5, 6, 7, 8, 9, 10, 11, 12, 13, 14, 15, or more target transgenes), wherein the plurality of target transgenes comprises the combination of transgenes, each target transgene comprising an upstream activating sequence, wherein the target transgenes are unlinked and in a hemizygous state; obtaining a second parental plant, wherein the second parental plant is isogenic and the second parental plant comprises an activator transgene, the activator transgene encoding a polypeptide comprising a DNA binding domain fused to a transcription activation domain, wherein the DNA binding domain binds to the upstream activating sequence; sexually crossing the first and second parental plants to produce the collection of seeds. This document also features a collection of seeds produced by such a method.

This document also features a method of identifying a combination of transgenes that improves a phenotypic feature of an organism. The method includes obtaining a first parental organism, the first parental organism comprising one or more target transgenes (e.g., 2, 3, 4, 5, 6, 7, 8, 9, 10, 11, 12, 13, 14, 15, or more target transgenes), wherein the target transgene comprises an upstream activating sequence; obtaining a second parental organism, the second parental organism comprising an activator transgene, the activator transgene encoding a polypeptide comprising a DNA binding domain fused to a transcription activation domain, wherein the DNA binding domain binds to the upstream activating sequence, wherein when the first parental organism contains one target transgene, the second parental organism also comprises at least one target transgene, and wherein the first or the second parental organism is hemizygous; sexually crossing the first and second parental organisms to produce a progeny population comprising a plurality of target transgenes; and identifying the combination of target transgenes that improves the phenotypic feature in the progeny population. The plurality of transgenes can be unlinked. The first and second parental organisms can be hemizygous. In some cases, the first parental organism includes two or more target transgenes (e.g., 2, 3, 4, 5, 6, 7, 8, 9, 10, 11, 12, 13, 14, 15, or more target transgenes) and the second parental organism does not include a target transgene. The first parental organism can include three or more or four or more target transgenes (e.g., 4, 5, 6, 7, 8, 9, 10, 11, 12, 13, 14, 15, or more target transgenes). In some cases, the first parental organism comprises one target transgene and the second parental organism comprises one or more target transgenes. In some cases, the second parental organism comprises a plurality of hemizygous activator transgenes having identical polypeptides under control of different promoters (e.g., wherein the different promoters are other than broadly expressing promoters).

This document also features a method of identifying a combination of transgenes that improves a phenotypic feature of an organism. The method includes obtaining a first parental organism, the first parental organism comprising a plurality of target transgenes, wherein each of the plurality of target transgenes comprises an upstream activating sequence; obtaining a population of second parental organisms, the second parental organisms comprising alternate activator transgenes, each activator transgene encoding a polypeptide comprising a DNA binding domain fused to a transcription activation domain, wherein the DNA binding domain binds to the upstream activating sequences, wherein the activator transgenes have identical polypeptides under control of different promoters, and wherein the alternate activator transgenes are essentially allelic; sexually crossing the first and second parental organisms to produce a progeny population; and identifying the combination of target transgenes that improves the phenotypic feature in the progeny population.

In another aspect, this document features a method of identifying a combination of transgenes that improves a phenotypic feature of a plant. The method includes selecting a plurality of target transgenes, each target transgene comprising an upstream activating sequence; obtaining a first parental plant, wherein the first parental plant is isogenic and the first parental plant comprises the plurality of target transgenes, wherein the target transgenes are unlinked and in a hemizygous state; obtaining a second parental plant, wherein the second parental plant is isogenic and the second parental plant comprises an activator transgene, the activator transgene encoding a polypeptide comprising a DNA binding domain fused to a transcription activation domain, wherein the DNA binding domain binds to the upstream activating sequence; sexually crossing the first and second parental plants to produce a progeny population; and scoring the phenotypic feature in individuals of the progeny population to identify the combination of transgenes.

This document also features a method of identifying a combination of transgenes that improves a phenotypic feature of a plant. The method includes obtaining a first parental plant, wherein the first parental plant is isogenic and the first parental plant comprises a plurality of target transgenes (e.g., four or more target transgenes), each target transgene comprising an upstream activating sequence; obtaining a second parental plant, wherein the second parental plant is isogenic and the second parental plant comprises a plurality of activator transgenes (e.g., four or more activator transgenes), the plurality of activator transgene encoding a polypeptide comprising a DNA binding domain fused to a transcription activation domain, wherein the DNA binding domain binds to the upstream activating sequence, and wherein the activator transgenes are unlinked and in a hemizygous state; sexually crossing the first and second parental plants to produce a progeny population; and scoring the phenotypic feature in individuals of the progeny population to identify the combination of transgenes. The plurality of target transgenes can be in a homozygous state.

In any of the methods described herein, the organism can be a plant. For example, the plant can be a member of a species selected from the group consisting of *Brassica, Carthamus, Glycine, Gossypium, Helianthus, Jatropha, Parthenium, Populus, Ricinus, Elaeis, Festuca, Hordeum, Lolium, Oryza, Panicum, Pennisetum, Phleum, Poa, Saccharum, Secale, Sorghum, Triticosecale, Triticum*, and *Zea*. For example, the plant can be *Panicum virgatum, Sorghum bicolor, Miscanthus giganteus, Zea mays, Glycine max, Brassica napus, Triticum aestivum, Gossypium hirsutum, Oryza sativa, Helianthus annuus, Medicago sativa, Beta vulgaris*, or *Pennisetum glaucum*. In any of the methods, the first plant can be male sterile. A male sterile plant can express a barnase polypeptide. The first plant can be cytoplasmic male sterile. The second plant can include a fertility restorer. The fertility restorer can be a barstar polypeptide.

In any of the methods described herein, the first and/or second parental organism further can include a homozygous transgene.

In any of the methods, the first parental organism and/or the second parental organism can be of an elite line.

In any of the methods, the plurality of target transgenes can include four or more target transgenes, e.g., 4, 5, 6, 7, 8, 9, 10, 11, 12, 13, 14, 15, or more target transgenes.

In any of the methods, the second parental plant can include two or more activator transgenes, e.g., 2, 3, 4, 5, 6, 7, 8, 9, 10, 11, 12, 13, 14, 15, or more activator transgenes.

In any of the methods, the plurality of target transgenes can include two to six different upstream activating sequences (UAS), wherein each target transgene contains one UAS; and wherein the second parental organism comprises a plurality of the hemizygous activator transgenes, wherein the plurality of activator transgenes encodes two to six different DNA binding domains, wherein each DNA binding domain binds to a different UAS. The plurality of transgenes can include four different upstream activating sequences such as the Hap1, Gal4, Leu3, and Ppr1 upstream activating sequences.

In any of the methods, the second parental organism can include two different hemizygous activator transgenes, each activator transgene encoding the polypeptide, wherein one hemizygous activator transgene comprises a first promoter operably linked to a nucleic acid sequence encoding the polypeptide, wherein the other hemizygous activator transgene comprises a second promoter operably linked to the nucleic acid sequence encoding the polypeptide, wherein the first and second promoters are different, and wherein the two different activator transgenes are linked. For example, the first promoter can be a root specific promoter, maturing endosperm promoter, embryo sac/early endosperm promoter, ovary tissue promoter, embryo promoter, photosynthetic tissue promoter, vascular tissue promoter, stem promoter, shoot-preferential promoter, callus-preferential promoter, trichome cell-preferential promoter, guard cell-preferential promoter, tuber-preferential promoter, parenchyma cell-preferential promoter, or senescence-preferential promoter. For example, the second promoter can be a ubiquitously expressing promoter.

In any of the methods, the target transgenes can be essentially allelic. The transgenes can be linked within about 1 cM or about 2 cM.

In any of the methods, identifying the combination of transgenes can include (i) phenotyping the progeny population to identify individuals having improved phenotypic performance and/or (ii) genotyping individuals (e.g., individuals identified in (i)) to identify the combination of transgenes. Phenotyping can include, for example, determining heterosis, grain yield, tolerance to abiotic stress (e.g., drought stress, osmotic stress, or nitrogen deficiency), tolerance to density stress, or seed oil content. Phenotyping can be a field performance test and/or a greenhouse test. Leaf punches from individuals can be genotyped. In some cases, genotyping of leaf punches is used to select a subset of individuals from the progeny population. In some cases, identifying the combination includes using seed chipping to select a subset of individuals from the progeny population.

This document also features a collection of seeds comprising a progeny population made by any of the methods described herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DETAILED DESCRIPTION

Figure 1:
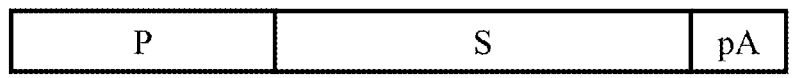
FIG. 1A is a schematic of a direct fusion construct, where a plant promoter (P) is operably linked to a sequence (S) to be transcribed. The sequence to be transcribed often is followed by a 3' polyadenylation site (pA).
FIG. 1B is a schematic of the two vectors of a two component system. For the male component, a promoter such as a tissue specific promoter (TSP) is operably linked to a nucleic acid sequence encoding an activation polypeptide that includes a DNA binding domain (e.g., the Gal4 DNA binding domain) fused to a transcriptional activation domain (e.g., the VP16 transcriptional activation domain). The female component has an upstream activating sequence (UAS4) followed by a minimal plant promoter (TATA) and the sequence to be transcribed (Target ORF). As with the direct fusion construct, the target ORF can be followed by a 3' polyA addition site (pA). The DNA binding domain of the activation polypeptide is capable of specifically binding to the UAS of the female component and activating transcription of the target ORF. In the absence of the activation polypeptide, the target transgene does not express the target sequence and thus causes no transgenic phenotype.
Figure 1:
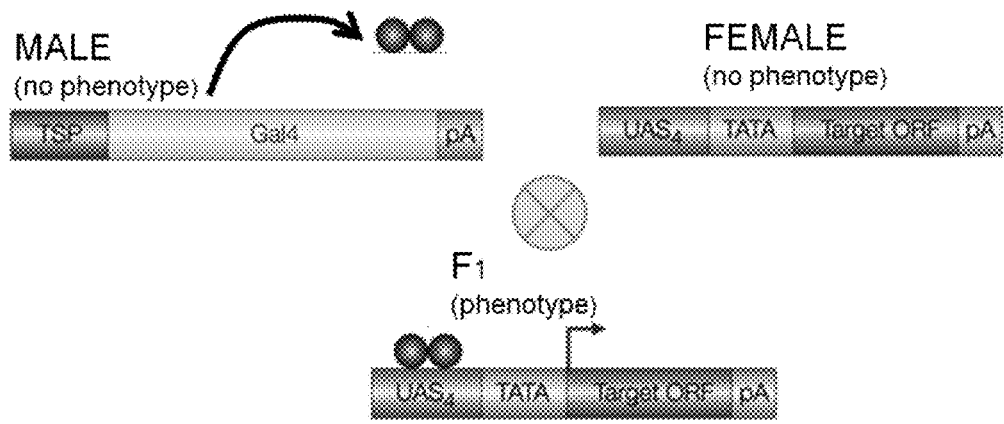

This document relates to methods and materials for identifying or optimizing combinations of transgenes or their overexpression patterns that improve one or more phenotypic features of an organism. For example, the methods described herein can be used in plants to improve grain yield; tolerance to an abiotic stress such as drought stress, osmotic stress, or nitrogen deficiency; soil aluminum; cold stress; frost stress; density stress; heat stress; oxidative stress; low light tolerance; herbicide stress; as well as improved water use efficiency; nitrogen use efficiency; phosphate use efficiency; seed oil or protein content; lignin content; biotic or pest resistance; biomass; heterosis; chemical composition such as higher percentage of sucrose; plant architecture such as increased tillering or branching, decreased or increased apical dominance, or increased root mass; flowering time; and/or biofuel conversion properties in a plant. "Water use efficiency," "nitrogen use efficiency," or "phosphate use efficiency" refers to increased yield under the same levels of input, i.e., same level of water, nitrogen, or phosphate.

In general, the methods described herein can include obtaining first and second parental organisms, wherein at least one of the parents includes a plurality of transgenes, sexually crossing the parent organisms to produce a progeny population, and identifying the combinations of transgenes that improve a phenotypic feature. In some cases, one of the parental organisms can be a non-transgenic plant. In some cases, each parent can be transgenic and can include one or more transgenes. As described in more detail below, the first and/or second parental organisms can be hemizygous for the transgene(s), and the gametes of the first or second parental organism can include independently segregating subgroups of the plurality of transgenes. By hemizygous it is generally meant an individual or a genetic state having or characterized by a transgenic sequence present in one chromosome but having no allelic counterpart.

The methods described herein provide a number of advantages when compared to alternative solutions, although not all advantages may be present in a specific embodiment.

For most breeding objectives, commercial breeders work within germplasm that is often referred to as the cultivated type. This germplasm is easier to breed with because it generally performs well when evaluated for agronomic performance. The performance advantage the cultivated type provides is sometimes offset by a lack of allelic diversity. This is the tradeoff a breeder accepts when working with cultivated germplasm: better overall performance, but a lack of allelic diversity. Breeders generally accept this tradeoff because progress is faster when working with cultivated material than when breeding with genetically diverse sources.

In contrast, when a breeder makes either intra-specific crosses, or inter-specific crosses, a converse trade off occurs.

In these examples, a breeder typically crosses cultivated germplasm with a non-cultivated type. In such crosses, the breeder can gain access to novel alleles from the non-cultivated type, but may have to overcome the genetic drag associated with the donor parent. Because of the difficulty with this breeding strategy, this approach often fails because of fertility and fecundity problems. The difficulty with this breeding approach extends to many crops, and is exemplified with an important disease resistant phenotype that was first described in tomato in 1944 (Smith, *Proc. Am. Soc. Hort. Sci.* 44:413-16). In this cross, a nematode disease resistance was transferred from *L. peruvianum* into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent. This allows the remaining genetic drag to be masked.

Some phenotypes are determined by the genotype at one locus. These simple traits, like those studied by Gregor Mendel, fall in discontinuous categories such as green or yellow seeds. Most variation observed in nature, however, is continuous, like yield in field corn, or human blood pressure. Unlike simply inherited traits, continuous variation can be the result of polygenic inheritance. Loci that affect continuous variation are referred to as quantitative trait loci (QTLs). Variation in the phenotype of a quantitative trait is the result of the allelic composition at the QTLs and the environmental effect. The heritability of a trait is the proportion of the phenotypic variation attributed to the genetic variance. This ratio varies between 0 and 1.0. Thus, a trait with heritability near 1.0 is not greatly affected by the environment. Those skilled in the art recognize the importance of creating commercial lines with high heritability agronomic traits because these cultivars will allow growers to produce a crop with uniform market specifications.

Consequently, transgenes conferring improved agronomic traits are a powerful tool in the development of new and improved cultivars. Transgenes are defined genetic alterations that do not require segregation from linked regions in order to avoid genetic drag. And again due to their genetic nature, contributions of transgenes to a defined trait have high heritability. As explained in more detail below, however, the precise impact of a transgene or combination of transgenes needs to be experimentally measured to understand the extent to which it depends on the relevant QTLs present in the germplasm in which they are tested. Understanding any QTL-dependent transgene impact is helpful, for instance, in cases where a transgene has a phenotypic effect in a heterotic genetic background that is significantly different in magnitude from the corresponding effect in plants with inbred depression.

Exploring the transgenic effect of many stacked transgenes, rather than single transgenes, is more likely to result in finding transgenic alterations resulting in significant yield or quality improvements. The genome of cultivated plants, for example, provides a genetic engineer with a background system of complex molecular interactions. For a transgene to boost a trait its products need to fit into the complex, regulated downstream networks appropriately. If the genetic background changes then the effect of the transgene may change too. For this reason specific transgenes sometimes fail to achieve the desired effect in all genetic backgrounds and environments. A change to a single component of a very complex system is unlikely to have a dramatic positive effect; several distinct alterations, on the other hand, as with a stack of transgenes, are more likely to result in an enhanced or synergistic positive effect, and/or diminished negative features of a transgene-caused phenotype. Moreover, unlike first-generation transgenes which generally necessitate high levels of ubiquitous overexpression, the expression pattern and levels of second-generation plant transgenes can be critical. This is because, while the first generation plant transgenes works by interacting with external factors like herbicides or pests, the second generation works by modulating the internal genetic and physical structure, with all its nuanced complexity of feedback and crosstalk between various physiological and molecular mechanisms. Hence, in addition to the selection of sequences to be expressed, their expression regulation, levels, and tissue specificity are important.

The methods described herein make it possible to produce and test in parallel a high number of transgenic sequences and/or promoters driving expression of transgenes. Any transgenic phenotype could be affected by a large number of transgene candidates, and a much larger number of combinations of transgene candidate stacks. The number of different combinations becomes significantly higher if different promoter-coding sequence candidates are also to be tested. But the phenotype of individual combinations, which may or may not turn out to be additive or even synergistic when compared to the phenotype of single transgenes, is generally unpredictable, so testing a large number of combinations is necessary. Hence, the high-throughput methods described herein are useful for quickly sorting through large numbers and identifying the combinations of transgenes that improve one or more phenotypic features.

Making new transgenic plants, while routinely accomplishable, is also a process that by its nature adds challenges to studying comparative performance of transgenic plants. This is because positional effects generally create a range of transgenic phenotypes in independently transformed plants. Many independent transformants need to be studied then to understand the potential impact of a transgene. Hence, compared to use of molecular stack vectors, the procedures described here require a limited number of selected transformation events, which cuts down on the amount of labor necessary to make and characterize the materials, but more importantly provides results such that the relative performance of recombined transgenic stacks can be reliably scored. Moreover, transgenic plants with individual components of a two-component system are "recyclable", i.e. once made and characterized they are likely to find use in multiple seasons and experimental setups. For example, activator transgenes with interesting promoter expression patterns only need to be made once, and then they can be used repeatedly with many different candidate target sequences, and need to be introgressed only once into parental any germplasm of interest. This feature is especially convenient for testing in elite germplasm because of the added effort require to introgress any transgene into a uniform and commercially relevant genetic background. Consequently, in some embodiments the methods presented allow optimization of stack transgenic phenotypes directly in elite backgrounds by testing a large numbers transgenes made by combining a limited number of good transformation events.

Analysis of second generation transgenes has been hampered by phenotype dependence on germplasm and environment. Model species and various screening assays have yielded many individual transgene candidates of interest, but their commercial feasibility is often not compelling when tested for field performance in elite crop germplasm under typical cultivation conditions.

In many cases, testing populations are made based on isogenic backgrounds so as to eliminate background genetic noise that would otherwise confound data interpretation. But in other cases, especially when the transgenic effect of a limited number of transgene combinations is to be understood, the genetic background may be intentionally diverse. For example, a promising stack of transgenes could be observed for performance in a segregating F2 population and subsequent generations, thus allowing selection and production of non-transgenic parents capable to perform especially well in the presence of a transgenic stack.

Using the presented methods, a phenotypic measurement can be the yield of harvestable material under typical field cultivation conditions, i.e. without an intentionally applied selection pressure. This data is certainly relevant from a product performance perspective, for identifying undesirable stack interactions, and when stacking transgenes affecting different traits that cannot be revealed by a single assay. But in addition, while some transgenes or stacks provide a survival or yield advantage under high selection pressure, they are known to otherwise have a negative impact when grown under typical cultivation conditions. Moreover, the populations of plants produced by the present methods are well-suited for comparative studies of related combinations. When testing side-by-side sibling plants that are otherwise genetically uniform but differ only with regard to having distinct combinations of a limited original pool of transgenic expressed sequences, and/or promoters that drive the expression, stacks of outstanding phenotypic impact can be readily identified. In some embodiments, populations produced according to the methods provided herein can be tested for field performance similarly to screening of segregating populations by plant breeders. This approach is a marked improvement over use of replicated plots for phenotyping defined single or stacked transgenics, in that a very high number of recombined transgenic genotypes can be compared through a process more reminiscent of breeding selections than transgenic characterization. This way, the effect of high numbers of transgene stack combinations can be simultaneously observed, often in a commercially relevant, elite genetic background, which may be made up of defined heterotic groups and/or QTLs for specific traits, and so well-performing stacks that surpass commercially relevant thresholds can be more easily identified. By using the methods described herein, useful transgene combinations and/or their differential expression become self-revealing, circumventing the general phenotypic unpredictability of specific individual stacks.

Transgenes

By transgene it is generally meant a vector present in a transgenic organism, having an engineered DNA sequence. Its presence in the transgenic organism can cause transcription of a part of its sequence. As such, a transgene may be a construct made up of a promoter upstream of and driving transcription of a DNA sequence of interest as depicted in FIG. 1A; but a transgene may also denote an equivalent molecular and phenotypic effect produced by operation of two distinct vectors present in the same cell, i.e. a two-component system, in which a promoter-containing activator component directs transcription of a DNA sequence of interest present in a target component as depicted in FIG. 1B.

The methods described herein are based in part on identifying combinations of different transgenes such as combinations of two to twenty transgenes that improve a phenotypic feature in an organism. For example, combinations of 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 3 to 15, 4 to 15, 5 to 15, 6 to 15, 7 to 15, 8 to 15, 9 to 15, 10 to 15, 11 to 15, 12 to 15, 13 to 15, 14 to 15, 2 to 10, 3 to 10, 4 to 10, 5 to 10, 6 to 10, 7 to 10, 8 to 10, or 9 to 10 transgenes can be used. Thus, a transgenic plant described herein can include two or more transgenes, e.g., three, four, five, six, seven, eight, nine, ten, eleven, twelve, thirteen, fourteen, fifteen, sixteen, seventeen, eighteen, nineteen, or twenty transgenes.

For plants, transgene candidates can be selected from a number of sources, including full length plant coding sequences or microRNAs retrievable from public databases such as GenBank or EMBL. In addition, many plant transgenes have been shown to alter important phenotypes when overexpressed and therefore can be used as target transgenes in the methods described herein. See, for example, U.S. Pat. Nos. 8,481,814; 8,471,099; 8,324,454; 8,222,482; 8,362,322; 8,344,210; 8,299,320; 8,222,482; 8,076,535; 8,049,068; 8,022,273; 7,8814,261; 7,803,983; 7,244,879; U.S. Patent Publication 20130014292; 20120297505; 20130125263; 20110061122; 20090304901; 20090172840; 20110061124; 20110265199; 20110179529; 20130191943; and 20130174298. There also are many publications and patents that provide examples of plant genes that can be used as target transgenes as described herein. See, for example, U.S. Patent Publication Nos. 20060041961; 20060075522; 20070294782; 20080148432; 20080295196; 20080301839; 20080050820; 20090031451; 20090044288; 20090070897; 20090100536; 20090144847; 20090144849; 20100017904; 20090293154; 2010015407; 20110119791; 201101263231; 20110197315; 20120060234; and 20140059714; U.S. Pat. Nos. 7,521,597; 7,485,775; 7,1667,67; 7,193,129; 7,196,245; and 7,223,904, and international publications WO201075143; WO2009009142; WO2010039750; WO20090134339; WO2007064724; WO2006045829; WO2008062049; WO2008092910; WO2007011681; and WO2007144190. In selecting combinations of transgenes to be tested, suitable sequences for either overexpression or inhibition also can be found in the technical literature related to biochemical or signaling pathways of interest, as well as based on co-expression studies and homology searches. In some embodiments, non-plant transgenes, such as insect resistance genes from *Bacillus thuringiensis*, also could be used in the methods described herein.

In some embodiments, the methods are applied to expressed sequences with insecticidal activity. Any known insecticidal protein-expressing transgenes can be used in the disclosed system, and they may be combined with other insecticidal expressed sequences (see, for example, Nanasaheb et al., *Toxins,* 2012, 4, 405-429; Schünemann et al., *ISRN Microbiol.,* 2014, Article ID 135675; U.S. Patent Application Publication No. 20140080755; U.S. Patent Application Publication No. 20140013471; and U.S. Pat. No. 8,569,583). Especially when sequences to be stacked exhibit some level of phytotoxicity, such as with insecticidal proteins, the expressed sequences can be fused to different organelle targeting signaling sequences. Consequently, their co-expression is less likely to result in increased cellular toxicity. In addition, seeking promoters with restricted expression patterns using the described methods can further improve the efficacy of insecticidal stacks while minimizing their toxicity. As pests generally feed on many different plant tissues and corresponding cellular organelles, stacks of insecticidal proteins are likely to be effective even when expression is limited to some plant tissues. Yet, limiting cellular co-expression diminishes the phytotoxicity of the stacks. Consequently, the disclosed methods can be used to find stacks of insecticidal transgenes most effective against pests of concern, while minimizing negative consequences to the host transgenic plants.

A transgene used in the methods described herein can be referred to as an "exogenous" nucleic acid as the transgene is either part of a recombinant nucleic acid construct and/or is not in its natural environment. For example, an exogenous nucleic acid can be a sequence from one species introduced into another species, i.e., a heterologous nucleic acid. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid. The plant genes can be native to the species of interest or can be heterologous to the species of interest.

In some embodiments, a regulatory region, intron, or coding region of an endogenous gene is replaced with a transgene described herein. Endogenous nucleic acids can be modified by homologous recombination techniques. For example, sequence specific endonucleases (e.g., zinc finger nucleases (ZFNs)) and meganucleases can be used to stimulate homologous recombination at endogenous plant genes. See, e.g., Townsend et al., *Nature* 459:442-445 (2009); Tovkach et al., *Plant J.*, 57:747-757 (2009); and Lloyd et al., *Proc. Natl. Acad. Sci. USA*, 102:2232-2237 (2005). CRISPR-Cas (Xie and Yang, *Mol. Plant* 2013, 6:1975-1983) and TALEN (Zhang et al., *Plant Physiology* 2013 161:20-27) genome editing techniques also can be used to replace an endogenous nucleic acid.

Target transgenes useful in the methods described herein can have a vector backbone. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen® (Madison, Wis.), Clontech® (Palo Alto, Calif.), Stratagene® (La Jolla, Calif.), and Invitrogen/Life Technologies® (Carlsbad, Calif.). Each transgene can be present on the same nucleic acid construct or can be present on separate nucleic acid constructs as described herein.

The vectors provided herein can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin) or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

Typically, the transgene used in the methods described herein includes a sequence to be expressed operably linked in sense orientation to one or more regulatory regions. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation sequence (UAS). For example, a suitable enhancer can be a cis-regulatory element (-212 to -154) from the upstream region of the octopine synthase (ocs) gene. Fromm et al., *The Plant Cell*, 1:977-984 (1989). In embodiments in which multiple regulatory regions are used, the regulatory region can be the same or can be different.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given target polypeptide can be modified such that optimal expression in a particular plant species is obtained, using appropriate codon bias tables for that species.

The choice of regulatory regions to be included in a recombinant construct depends upon several factors, including, but not limited to, efficiency, selectability, inducibility, desired expression level, and cell- or tissue-preferential expression. Some regulatory regions initiate transcription only, or predominantly, in certain cell types. Methods for identifying and characterizing regulatory regions in plant genomic DNA include, for example, the methods described in Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. The sequences of the regulatory regions indicated below as well as additional regulatory regions are described in more detail in U.S. Patent Application Serial Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; PCT/US07/62762; PCT/US2009/032485; and PCT/US2009/038792.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, YP0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOs-MEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A plant promoter can be a "broadly expressing" plant promoter when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in a transgene provided herein include the p326, YP0144, YP0190, p13879, YP0050, p32449, 21876, YP0158, YP0214, YP0380, PT0848, and PT0633 promoters. Additional examples of broadly expressing promoters that can be used as described herein include, without limitation, the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter.

Additional non-limiting examples of broad promoters that can be used in a transgene described herein is the sequence of regulatory region PD3141 set forth in the sequence listing of PCT/US2009/032485, the sequence of regulatory region p326 set forth in the sequence listing of U.S. application Ser. No. 10/981,334, or the the sequence of regulatory region PD2995 (a 600 bp version of p326) set forth in the sequence listing of PCT/US2009/32485.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Non-limiting examples of root-preferential promoters that can be used in transgenes described herein include the YP0128, YP0275, PT0625, PT0660, PT0683, and PT0758 promoters. Other examples root-preferential promoters that can be used include the PT0613, PT0672, PT0688, and PT0837 promoters, which drive transcription primarily in root tissue and to a lesser extent in ovules and/or seeds. Other examples of root-preferential promoters that can be used include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990), and the tobacco RD2 promoter.

Another example of a root promoter that can be used is the sequence of regulatory region PD3561 set forth in the sequence listing of PCT/US2009/038792. Therein, the expression pattern of the PD3561 regulatory region is described for T0 rice plants overexpressing a construct comprising PD3561 driving expression of EGFP. Expression was observed in roots of seedlings in the cortex, epidermis, and vascular tissues. In mature plants, expression was observed strongly throughout the root with the exception of the root cap and in the cortex, epidermis, and vascular tissues.

iii. Maturing Endosperm Promoters

In some embodiments, promoters that drive transcription in maturing endosperm can be useful in a transgene. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the transgenes provided herein include the napin promoter, the Arcelin-5 promoter, the phaseolin promoter (Bustos et al., *Plant Cell*, 1(9):839-853 (1989)), the soybean trypsin inhibitor promoter (Riggs et al., *Plant Cell*, 1(6):609-621 (1989)), the ACP promoter (Baerson et al., *Plant Mol. Biol.*, 22(2):255-267 (1993)), the stearoyl-ACP desaturase promoter (Slocombe et al., *Plant Physiol.*, 104(4):167-176 (1994)), the soybean $\alpha'$ subunit of $\beta$-conglycinin promoter (Chen et al., *Proc. Natl. Acad. Sci. USA*, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable for use in a transgene are the Osgt-1 promoter from the rice glutelin-1 gene (Zheng et al., *Mol. Cell Biol.*, 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful in the transgenes described herein, e.g., a polygalacturonidase promoter, the banana TRX promoter, the melon actin promoter, YP0396, and PT0623. Non-limiting examples of promoters that can be used are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression of a transgene in the embryo sac/early endosperm, a regulatory region can be used that is active in polar nuclei and/or the central cell, or in precursors to polar nuclei, but not in egg cells or precursors to egg cells. For example, promoters that drive expression only or predominantly in polar nuclei or precursors thereto and/or the central cell can be used in the transgenes described herein. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Non-limiting examples of promoters that can be used in transgenes described herein include those derived from the following genes: *Arabidopsis* viviparous-1 (see, GenBank No. U93215); *Arabidopsis* atmyc1 (see, Urao, *Plant Mol.*

Biol., 32:571-57 (1996); Conceicao, *Plant*, 5:493-505 (1994)); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that can be used in a transgene include those derived from the following genes: maize MAC1 (see, Sheridan, *Genetics*, 142: 1009-1020 (1996)); maize Cat3 (see, GenBank No. L05934; Abler, *Plant Mol. Biol.*, 22:10131-1038 (1993)). Other non-limiting examples of promoters that can be used include the following *Arabidopsis* promoters: YP0039, YP0101, YP0102, YP0110, YP0117, YP0119, YP0137, DME, YP0285, and YP0212 or the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. For example, promoters that preferentially drive transcription in early stage embryos prior to the heart stage can be used in a transgene as well as promoters that drive transcription in late stage and maturing embryos. Non-limiting examples of embryo-preferential promoters that can be used include the barley lipid transfer protein (Ltp1) promoter (*Plant Cell Rep* 20:647-654 (2001)), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. For example, a promoter that drives expression only or predominantly in such tissues can be used in the transgenes described herein. Non-limiting examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104: 997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other non-limiting examples of photosynthetic tissue promoters that can be used include PT0535, PT0668, PT0886, YP0144, YP0380 and PT0585.

viii. Vascular Tissue Promoters

Non-limiting examples of promoters that can be used in a transgene that have high or preferential activity in vascular bundles include YP0087, YP0093, YP0108, YP0022, and YP0080. Other examples of vascular tissue-preferential promoters that can be used include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2): 185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Non-limiting examples of drought-inducible promoters that can be used in a transgene include YP0380, PT0848, YP0381, YP0337, PT0633, YP0374, PT0710, YP0356, YP0385, YP0396, YP0388, YP0384, PT0688, YP0286, YP0377, PD1367, and PD0901. Non-limiting examples of nitrogen-inducible promoters that can be used include PT0863, PT0829, PT0665, and PT0886. Non-limiting examples of shade-inducible promoters that can be used include PR0924 and PT0678. A non-limiting example of a salt-inducible promoter that can be used is rd29A (Kasuga et al. (1999) *Nature Biotech* 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Non-limiting examples of stem promoters that can be used in a transgene include YP0018 which is disclosed in US20060015970 and CryIA(b) and CryIA(c) (Braga et al. 2003, *Journal of New Seeds* 5:209-221).

xii. Other Promoters

Other classes of promoters that can be used in a transgene include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

In some cases, more than one regulatory region may be present in a recombinant polynucleotide, e.g., introns, enhancers, upstream activation regions, transcription terminators, and inducible elements. For example, more than one regulatory region can be operably linked to the sequence of a polynucleotide encoding a target polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

In some cases, a transgene can inhibit one or more functions of an endogenous polypeptide. For example, a transgene can include a nucleic acid that encodes a dominant negative polypeptide, which can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., U.S. Publication No. 20070056058. As another example, a point mutation that results in a non-conservative amino acid substitution in a catalytic domain can result in a dominant negative polypeptide. See, e.g., U.S. Publication No. 2005032221. As another example, a dominant negative polypeptide can be a transcription factor that is truncated relative to a native wild type transcription factor, such that the truncated polypeptide retains the DNA binding domain(s) but lacks the activation domain(s), and possibly comprises a repression domain (see Hiratsu et al, 2003, Plant J. 34:733-739). Such a truncated polypeptide can inhibit the wild type transcription factor from binding DNA, thereby inhibiting transcription activation.

In some embodiments, one or more of the transgenes used in the methods described herein inhibit expression of a polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); and *Nature Reviews RNA interference collection*, October 2005 on the World Wide Web at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding target polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method to inhibit gene expression. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method of inhibiting gene expression, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA,* 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a target polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the target polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a target polypeptide, and the other strand of the stem portion of the double stranded RNA comprises a sequence that is similar or identical to the sequence that is complementary to the 3' or 5' untranslated region, respectively, or a fragment thereof, of the mRNA encoding the target polypeptide. In other embodiments, one strand of the stem portion of a double stranded RNA comprises a sequence that is similar or identical to the sequence of an intron, or a fragment thereof, in the pre-mRNA encoding a target polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publication Nos. 20030175965, 20030175783, 20040214330, and 20030180945.

Constructs containing regulatory regions operably linked to nucleic acid molecules in sense orientation also can be used to inhibit the expression of a gene. The transcription product can be similar or identical to the sense coding sequence, or a fragment thereof, of a target polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a target polypeptide, or a fragment of such sequences. In some embodiments, the sense or antisense sequence is identical or complementary to a sequence of the regulatory region that drives transcription of the gene encoding a target polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a target sequence. The sense sequence complementary to the antisense sequence can be a sequence present within the mRNA of the target polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. In some cases, a nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141:1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences or the left and right border-like sequences of the P-DNA flank, or are on either side of, the nucleic acid. See, U.S. Patent Publication No. 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

Species

The methods described herein can be applied to organisms capable of genetic modification and sexual recombination. For example, the methods described herein can be applied to plants (e.g., plant species of importance to agriculture), fungi (e.g., yeast), protozoans, and animals (e.g., fish such as salmon or zebra fish, fruit flies, or earthworms). In some cases, the methods described herein can be applied to monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

For example, suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hor-* deum, *Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*. In some embodiments, suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (*eucalyptus*), Triticosecale (*triticum*-wheat X rye) or bamboo.

Additional examples of suitable species include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea, Beta vulgaris* (sugarbeet), *Manihot esculenta* (cassava), *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum (Huperzia serrata), Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (*petunia*), *Poinsettia pulcherrima* (poinsettia), *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides, Pennisetum arnhemicum, Pennisetum caffrum, Pennisetum clandestinum, Pennisetum divisum, Pennisetum glaucum, Pennisetum latifolium, Pennisetum macrostachyum, Pennisetum macrourum, Pennisetum orientale, Pennisetum pedicellatum, Pennisetum polystachion, Pennisetum polystachion* ssp. *Setosum, Pennisetum purpureum, Pennisetum setaceum, Pennisetum subangustum, Pennisetum typhoides, Pennisetum villosum*, or hybrids thereof (e.g., *Pennisetum purpureum* x *Pennisetum typhoidum*).

In some embodiments, a suitable species can be a wild, weedy, or cultivated *Miscanthus* species and/or variety such as, but not limited to, *Miscanthus* x *giganteus, Miscanthus sinensis, Miscanthus* x *ogiformis, Miscanthus floridulus, Miscanthus transmorrisonensis, Miscanthus oligostachyus, Miscanthus nepalensis, Miscanthus sacchariflorus, Miscanthus* x *giganteus 'Amuri', Miscanthus* x *giganteus 'Nagara', Miscanthus* x *giganteus 'Illinois', Miscanthus sinensis* var. '*Goliath*', *Miscanthus sinensis* var. '*Roland*', *Miscanthus sinensis* var. '*Africa*', *Miscanthus sinensis* var. '*Fern Osten*', *Miscanthus sinensis* var. *gracillimus, Miscanthus sinensis* var. *variegates, Miscanthus sinensis* var. *purpurascens, Miscanthus sinensis* var. '*Malepartus*', *Miscanthus sacchariflorus* var. '*Robusta*', *Miscanthus sinensis* var. '*Silberfedher*' (aka. Silver Feather), *Miscanthus transmorrisonensis, Miscanthus condensatus, Miscanthus yakushimanum, Miscanthus* var. '*Alexander*', *Miscanthus* var. '*Adagio*', *Miscanthus* var. '*Autumn Light*', *Miscanthus* var. '*Cabaret*', *Miscanthus* var. '*Condensatus*', *Miscanthus* var. '*Cosmopolitan*', *Miscanthus* var. '*Dixieland*', *Miscanthus* var. '*Gilded Tower*' (U.S. Pat. No. 14,743), *Miscanthus* var. '*Gold Bar*' (U.S. Pat. No. 15,193), *Miscanthus* var. '*Gracillimus*', *Miscanthus* var. '*Graziella*', *Miscanthus* var. '*Grosse Fontaine*', *Miscanthus* var. '*Hinjo* aka *Little Nicky*'™, *Miscanthus* var. '*Juli*', *Miscanthus* var. '*Kaskade*', *Miscanthus* var. '*Kirk Alexander*', *Miscanthus* var. '*Kleine Fontaine*', *Miscanthus* var. '*Kleine Silberspinne*' (aka. '*Little Silver Spider*'), *Miscanthus* var. '*Little Kitten*', *Miscanthus* var. '*Little Zebra*' (U.S. Pat. No. 13,008), *Miscanthus* var. '*Lottum*', *Miscanthus* var. '*Malepartus*', *Miscanthus* var. '*Morning Light*', *Miscanthus* var. '*Mysterious Maiden*' (U.S. Pat. No. 16,176), *Miscanthus* var. '*Nippon*', *Miscanthus* var. '*November Sunset*', *Miscanthus* var. '*Parachute*', *Miscanthus* var. '*Positano*', *Miscanthus* var. '*Puenktchen*' (aka '*Little Dot*'), *Miscanthus* var. '*Rigoletto*', *Miscanthus* var. '*Sarabande*', *Miscanthus* var. '*Silberpfeil*' (aka. Silver Arrow), *Miscanthus* var. '*Silverstripe*', *Miscanthus* var. '*Super Stripe*' (U.S. Pat. No. 18,161), *Miscanthus* var. '*Strictus*', or *Miscanthus* var. '*Zebrinus*'.

In some embodiments, a suitable species can be a wild, weedy, or cultivated *sorghum* species and/or variety such as, but not limited to, *Sorghum almum, Sorghum amplum, Sorghum angustum, Sorghum arundinaceum, Sorghum bicolor* (such as bicolor, *guinea, caudatum, kafir*, and *durra*), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum* x *almum, Sorghum* x *sudangrass* or *Sorghum* x *drummondii*.

Thus, the methods described herein can be applied to a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (*sorghum, sudangrass*), *Mis-* canthus giganteus (miscanthus), Saccharum sp. (energycane), Populus balsamifera (poplar), Zea mays (corn), Glycine max (soybean), Brassica napus (canola), Triticum aestivum (wheat), Gossypium hirsutum (cotton), Oryza sativa (rice), Helianthus annuus (sunflower), Medicago sativa (alfalfa), Beta vulgaris (sugarbeet), or Pennisetum glaucum (pearl millet).

In certain embodiments, the methods described herein can be applied to hybrids of different species or varieties of a specific species (e.g., Saccharum sp. X Miscanthus sp., Sorghum sp. X Miscanthus sp., e.g., Panicum virgatum x Panicum amarum, Panicum virgatum x Panicum amarulum, and Pennisetum purpureum x Pennisetum typhoidum).

An elite plant line or elite plant variety can be an agronomically superior plant line that has resulted from many cycles of breeding and selection for superior agronomic performance. Generally, an elite variety is a collection of plants that has been selected for a particular characteristic or combination of characteristics or traits, uniform and stable in those characteristics, and when propagated by appropriate means, retains those characteristics. An elite variety may have a high uniformity level at least with respect to specific genomic regions. For example, at least 90% of the individuals of an elite variety may exhibit a specific genotypic profile, as it may be detected and characterized with the respective molecular markers. Numerous elite plant lines are available and known to those of skill in the art of breeding for any cultivated plants. Traits that may be considered to confer elitism include, without limitation, good lodging resistance, reduced bacterial infection susceptibility, good seed set, good pollen set, good roots, good cold germination, good combining ability, tolerance to pests, tolerance to disease, tolerance to drought, tolerance to salts or metals, uniform floral timing, good fertilizer use efficiency, high yield as an inbred, high yield as a hybrid, good plant height, and optionally herbicide resistance or tolerance. In some cases, an elite line or elite cultivar might not itself exhibit such traits, but rather it is considered elite because it exhibits the ability to serve as one parent of an elite hybrid.

Transformation

An organism provided herein can be transformed by having a transgene integrated into its genome, i.e., can be stably transformed. Stably transformed cells typically retain the introduced nucleic acid with each cell division. A plant or plant cell also can be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein. Techniques for introducing nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,538,880; 5,204,253; 6,329,571 and 6,013,863, Richards et al., Plant Cell. Rep. 20:48-54 (2001), and Somleva et al., Crop Sci. 42:2080-2087 (2002). If a cell or cultured tissue is used as the recipient tissue for transformation, plants can be regenerated from transformed cultures if desired, by techniques known to those skilled in the art.

Transgenic plant cells used in methods described herein can constitute part or all of a whole plant. Such plants can be grown in a manner suitable for the species under consideration, either in a growth chamber, in a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct. Often, a transgene can be repeatedly backcrossed to an inbred line (also called isogenic or near-isogenic) to generate an isogenic parent plant.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

Two Component System

In some cases, a two component system can be used in the methods described herein. In two component systems, two different transgenes are used, one is an activation transgene encoding an activation polypeptide and the other is a target transgene encoding the target sequence of interest. An activator transgene expresses an activation polypeptide (also can be referred to as a transcription factor) made up of a DNA binding domain fused to a transcription activation domain. A target transgene has an upstream activating sequence (UAS), which is specifically recognized by the DNA binding domain of the activation polypeptide, upstream of a minimal plant promoter and a target sequence. When present in the same cell, the activation polypeptide binds to the UAS, and the target sequence is transcribed. In the absence of an activation polypeptide, the target transgene does not express the target sequence and thus causes no transgenic phenotype. More than one activator and more than one target transgene may be stacked in the same parental line. When a parental line with an activator transgene is crossed with a parental line with a matching target transgene, i.e., the DNA binding domain of the activator can bind the UAS of the target, the hybrid will express the target sequence and therefore exhibit the phenotype conferred by the target sequence expression.

The DNA binding domain(s) and transcription activation domain(s) of the activation polypeptide can be synthetic or can be derived from different sources (i.e., be chimeric transcription factors). It is known that domains from different naturally occurring transcription factors can be combined in a single polypeptide and that expression of such a chimeric transcription factor in plants can activate transcription. In some embodiments, a chimeric transcription factor has a DNA binding domain derived from the yeast Gal4 gene and a transcription activation domain derived from the VP16 gene of herpes simplex virus. In other embodiments, a chimeric transcription factor has a DNA binding domain derived from a yeast HAP1 gene and the transcription activation domain derived from VP16. See, e.g., WO 97/30164.

A list of DNA binding domains from various transcription factors is shown in Table 1, along with their respective upstream activation sequences. These domains are suitable for use in a chimeric transcription factor in plants and other organisms. DNA-binding domains on this list have been expressed in transgenic plants as components of chimeric transcription factors. It is contemplated that the DNA binding domain from a *S. cerevisiae* LEU3 transcription factor and its associated UAS (CCG-N4-CGG, SEQ ID NO:1) and the DNA binding domain from a *S. cerevisiae* PDR3 transcription factor and its associated UAS (CCGCGG) will also be suitable. See, Hellauer et al., *Mol. Cell Biol.* (1996).

TABLE 1

Binding Domains

| Transcription Factor Name | Source Organism | UAS | Reference |
| --- | --- | --- | --- |
| GAL4 | *S. cerevisiae* | CGG-$N_{11}$-CCG (SEQ ID NO: 2) | Liang et al, Mol. Cell. Biol 1996, 16:3773-80; U.S. Pat. No. 6,255,558 |
| HAP1 | *S. cerevisiae* | agcaCGGacttatCGGtcgg (SEQ ID NO: 3) or gcagCGGtattaaCGGgattac (SEQ ID NO: 4) | WO 97/30164 |
| PPR1 | *S. cerevisiae* | CGGN$_6$CCG (SEQ ID NO: 5) (e.g., TCTTCGGCAATTGCCGAAGA, SEQ ID NO: 6) | Mamane et al JBC 1998, 273:18556-61 |
| LEU3p | *S. cerevisiae* | CCG N$_4$ CGG (SEQ ID NO: 1) (e.g., CCTGCGGGTACCGGCTTGG, SEQ ID NO: 7) | Hellauer et al. (1996) Mol. Cell. Biol. 16, 6096-6102; Mamane et al JBC 1998, 273:18556-61. |
| LexA | *E. coli* | TACTG(TA)$_5$CAGTA (SEQ ID NO: 8) | U.S. Pat. No. 6,399,857; U.S. Pat. No. 6,946,586; Wade et al, Genes & Dev. 19:2619-2630, 2005 |
| Lac Operon | *E. coli* | AATTGTGAGCGCTCACAATT (SEQ ID NO: 9) | Moore et al. PNAS Jan 6; 95(1):376-81 (1998); U.S. Pat. No. 6,172,279 |
| ArgR | *E. coli* | wNTGAAT-w$_4$-ATTCANw (SEQ ID NO: 10) | Werner K Maas, Microbiol Review, 1994 Vol 58, pp. 631-640 |
| AraC | *E. coli* | TATGGATAAAAATGCTA (SEQ ID NO: 11) | Bustos and Schleif, PNAS 1993, 90:5638-42 |
| Synthetic Zn proteins | N/A | N/A | U.S. Pat. No. 7,273,923; U.S. Pat. No. 7,262,054 |

A list of transcription activation domains from various transcription factors is shown in Table 2, along with the amino acid residues where the domain is located in the protein. These domains are suitable for use in a chimeric transcription factor in plants. Most of the activation domains on this list have been shown to be functional in heterologous plant systems.

TABLE 2

Activation Domains

| Transcription Factor Name | Organism | Domain Location (Amino Acid Residue Nos.) | Reference |
| --- | --- | --- | --- |
| C1 protein | Maize | 173-273 | Goff SA et al., *Gene & Dev.* (1991), Van Eenenaam et al. *Metab Eng.* (2004) |
| ATMYB2 | *Arabidopsis* | 146-269 | Urao et al., *Plant J.* (1996) |
| HAFL-1 | Wheat | 214-273 | Okanami et al. *Genes to Cells* (1996) |
| ANT | *Arabidopsis* | 221-274 | Krizek & Sulli, *Planta* (2006) |
| ALM2 | *Arabidopsis* | 203-256 | Anderson & Hanson, *BMC Plant Biol.* (2005) |
| AvrXa10 | *Xanthomonas oryzae* pv. *oryzae* | 133-274 | Zhu et al. *Plant Cell* 1999 |

TABLE 2-continued

Activation Domains

| Transcription Factor Name | Organism | Domain Location (Amino Acid Residue Nos.) | Reference |
|---|---|---|---|
| Viviparous 1 (VP1) | Maize | 134-213 | McCarty et al. *Cell* (1991) |
| DOF | Maize | 1-163 | Yanagisawaa & Sheen *Plant Cell* (1998) |
| RISBZ1 | Rice | 1060-1102 | Onodera et al., *J. Biol. Chem.* (2001) |
| VP16 | *Herpes simplex* | 411-490 | Greaves and O'Hare, *J. Virol.*, 63:1641-1650 (1989) |

In some embodiments described here, the activation polypeptide is used to activate transcription of a plurality of transgenes of interest. In some embodiments, two or more different activation polypeptides can be expressed such that each of the activation polypeptides activates at least one transgene of interest. Furthermore, each sequence of interest can have a different expression pattern. For example, each transcription factor can be linked to a different promoter such that each sequence can be expressed, for example, at a different developmental stage, in a different tissue (e.g., roots or leaves), or ubiquitously expressed.

In some embodiments, rather than having an activation domain, the component comprises a DNA binding domain fused to a repression domain (see Hiratsu et al, 2003, Plant J. 34:733-739). These repressor components eliminate or diminish expression of sequences linked to the corresponding UASs, and thus can be used in some embodiments to alter expression patterns and levels of activators.

Some embodiments comprise a third component working in conjunction with the two components described above. The third component is made up of a UAS of a first DNA binding domain specificity operably linked to a sequence to be expressed which encodes a DNA binding domain of a second specificity fused to an activation or repression domain. As such, the third component can be added in different applications. It can be useful in "translating" promoter activation expression from one DNA binding specificity to another that matches a target transgene UAS, as it may be needed or convenient in some situations. The third component may broaden the action of one activator transgene by simultaneously expressing one or more additional activator polypeptides capable of acting on different UASs, as it may be needed or convenient for specific methods. Many third components may also be used simultaneously. For example, they can form activation cascades, where each third component is capable of acting on other third components and/or target transgenes. Finally, some target transgenes or third components with repression domains can be directed to knock out expression of other target transgenes or third components. Use of third components can be designed so that they segregate in testing populations, thus providing more expression variability of the subject target transgenes.

Selection of Transgenic Inserts of Defined Linkage

In many of the methods described herein, genetically unlinked transgenes are used so that their genetic inheritance is random and segregation distortion effects can be avoided. For example, this is generally the case when many transgenes are to be rearranged in different combinations by meiotic recombination. Unlinked transgenes may be on different chromosomes, or may be on the same chromosome but distantly so that their recombination frequency is 50%. In some cases, linked transgenes can be used, either because it is convenient as when working with existing transformation events, or because it is desirable, such as when either stacking or avoiding stacking of specific transgene pairs is desirable. Linkage of transgenes, i.e. with a recombination frequency less than 50%, can then be taken into account if needed when calculating the distribution of genotypes in a population made with the linked transgenes.

In some embodiments, tight linkage and non-random segregation of selected transgene can be used. For example, for some methods, the presence in a testing population of either one of one of two alternative transgenes would be more informative than either the absence or presence of both. This would often be the case for activator lines of a two component system having two activator transgenes using the same DNA binding domain but driven by different promoters. Accordingly, a plant with two alternative activator transgenes that are tightly linked (e.g., within 1 cM or 2 cM) but inherited from different parents, i.e. hemizygous for the two linked transgenes, will pass along to progeny either one or the other of the alternative activator transgenes, and rarely both or neither.

Determining linkage of two different insertion events can be accomplished in many ways. One way is the classical genetic segregation analysis. Another way is determining linkage to specific markers that are well characterized for the specific organism. For organism with fully sequenced genomes, linkage or lack thereof can be known by determining the genomic insertion points of two specific transgenes.

As an alternative to random insertion of transgenes followed by linkage determination, transgene insertion could be targeted (see, for example, Cai et al., *Plant Mol Biol.* 2009 69(6):699-709) to maintain desired linkage relationships. For example, a vector could be made having two or more expression cassettes. Each expression cassette can include transgenes intended to be alternatively tested, such as activator transgenes under control of different promoters or target transgenes with different upstream activating sequences. Each transgene can be flanked its own set of recognition domain for zinc finger nucleases. Transgenes so flanked can be specifically deleted by expression of a zinc finger nuclease complementary to the recognition domain, followed by DNA repair, while the alternative transgenes would remain in the genome (see, for example, Petolino et al., *Plant Mol Biol.* 2010 73(6):617-628). Hence, essentially allelic alternative transgenes can be generated using such a method. They could then be crossed to make heterozygous parents. Of course, different designs can be envisioned, such as designing transgenes having many promoters separated by transcription insulators from the sequence to be expressed. Each insulator could be flanked by is specific zinc finger recognition domain, and so it could be removed by contact with a complementary zinc finger nuclease.

Alternatively, at an initial stage, a transgene would be made up of one or more zinc finger recognition domains. Subsequent transformations would target transgenes for insertion within the recognition domains (see for example, Shukla et al., *Nature* 2009 459:437-441).

Other genome editing or targeting options, such as CRISPR-Cas (Xie and Yang, *Mol. Plant* 2013, 6:1975-1983), RMCE (Li et al, Plant Physiology, 2009, 151:1087-095) and TALEN (Zhang et al., *Plant Physiology* 2013 161:20-27) can also be adapted to make essentially allelic transgenic inserts, for example, by deletion or inactivation by targeted mutation of transgene promoters or coding sequences.

Yet another option is incorporation of the 34 bp lox recombination site within a transformed transgene, thus enabling addition or deletion of other sequences at the respective chromosomal location using the CRE-LOX system (see, for example, Day et al., *Genes & Development* 2000 14:2869-2880).

Crossing

The methods described herein are based on segregation of hemizygous transgenes in sexual crossing. The recombination step often involves crossing of two different plants, i.e., male and female, rather than self-fertilization of self-compatible plants. Typically, hybrids can be produced by preventing self-pollination of female parent plants (i.e., seed parents), and permitting pollen from male parent plants to fertilize female parent plant, and allowing $F_1$ hybrid seeds to form on the female plants. Self-pollination of female plants can be prevented by physically emasculating the flowers at an early stage of flower development. Alternatively, pollen formation can be prevented on the female parent plants using a form of male sterility. For example, male sterility can be cytoplasmic male sterility (CMS), nuclear male sterility, genetic male sterility such as temperature or photoperiod-sensitive genetic male sterility, molecular male sterility wherein a transgene or mutation inhibits microsporogenesis and/or pollen formation, or be produced by self-incompatibility. Female parent plants containing CMS are particularly useful. Some crop species such as corn, *sorghum*, canola, and rice have well known hybridization systems based on cytoplasmic male sterility (CMS). In embodiments in which the female parent plants are CMS, the male parent plants typically contain a fertility restorer gene to ensure that the $F_1$ hybrids are fertile.

The parent plants can be grown as substantially homogeneous adjoining populations to facilitate natural cross-pollination from the male parent plants to the female parent plants. The $F_1$ seed formed on the female parent plants can be selectively harvested by conventional means. One also can grow the two parent plants in bulk and harvest a blend of $F_1$ hybrid seed formed on the female parent and seed formed upon the male parent as the result of self-pollination.

A hybridization system based on a two component design also can be adopted in species where CMS or physical emasculation options are not widely available. Accordingly, a line could be developed that is homozygous for a target transgene coding for the cytotoxic barnase sequence. A different line has an activator transgene with a DNA binding domain complementary to the UAS of the barnase target, and driven by an anther specific promoter. The two lines are crossed to produce the female for the cross needed to produce the testing population. The male plant for the cross which produces the testing population, on the other hand, is homozygous for a barnase-inactivating barstar sequence. The barstar transgene could be either a target transgene for a two component system, possibly with the same UAS as the barnase transgene, or could be a direct fusion gene. Of course, other transgenes would also be present in the male and female progenitors of the testing population. Alternatively, similarly to the canola MS8/RF3 hybridization system, male sterility can be achieved with a barnase sequence driven by a tapetum-specific promoter (Mariani et al., Nature 357, 384-387, 1992), which can be used in conjunction with a linked herbicide tolerance gene for female propagation.

Fertility can be restored when needed by crossing with a plant having a construct directing expression of barstar sequence in the same cells as the barnase. Suitable promoters may be found in the literature, including Kato et al., 2010 Plant Mol. Biol. Rep 28: 381-387, Luo et al., 2006 Plant Mol. Biol 62(3): 397-408, Gupta et al., 2007 Plant Cell Rep. 26(11): 1919-31, Liu et al., 2013 Planta 238(5): 845-57, and Goldberg et al., 1993 Plant Cell 5: 1217-1229.

Nevertheless, self-fertilization of a self-compatible species is also feasible to carry out the methods provided herein. Selfing of a plant with hemizygous genes can provide by meiotic recombination needed for a testing population. Selfing of hemizygous materials may also be performed at an earlier or intermediate step of providing a testing population to produce plants with a genetic composition of hemizygous and/or homozygous transgenes that may be desirable for phenotyping, producing, or propagating.

Transgene Mixing in Testing Populations

In some embodiments, each transgene in a hemizygous state will segregate during meiosis, forming gametes either containing or free of the transgene. This meiotic segregation is used in the methods provided herein, so that parental plants carrying many transgenes of interest generate progeny with many different combinations of the parental transgenes.

There are many ways in which parental plants having hemizygous transgenes of interest can be obtained. For example, for self-compatible species, it is easy to make by selfing and selection a parent stock that is homozygous for the transgenes of interest. Hemizygous transgenes will then result by crossing homozygous plants with a plant null for the respective transgenes. For self-incompatible species, fixing homozygous transgenes in a propagating population is also feasible, and molecular characterization of individual progenitors would be especially helpful. Creating double haploids can also be useful, if feasible for a particular species, when needed to obtain plants homozygous for desired transgenes.

In some embodiments testing populations are made by crossing parents with heterogeneous transgenic makeup. Crosses may be made randomly starting with parents of diverse but known transgene mixture composition. As long as pollination occurs randomly, the genetic structure of the progeny or testing population can be inferred from the distribution of transgenes in the parents. This approach may be convenient in certain cases, such as when working with obligate outcrossing species or with populations of improvement rounds.

The genetic background of a testing population is in many embodiments as homogenous as possible, so as to have as little individual to individual variation as possible, as this variation would interfere with the phenotype to be scored that is attributable to individual transgene combinations.

In some embodiments, the parent plants also can be homozygous for one or more transgenes such as a gene conferring herbicide resistance, a gene conferring insect resistance, or a combination of transgenes identified using the methods described herein.

In some embodiments, the parent plants are essentially allelic heterozygotes, as illustrated in Example 10.

In some embodiments, mixed transgenes are co-transformed, hemizygous transformant plants are regenerated, and then a testing population is made by sexual crossing the hemizygous co-transformants. In these cases, the transformation may be transient.

In some embodiments, transgenes of a two component system may be present in both the male and female parents of the cross that makes the testing population. For example, if all the activator transgenes are present in one parent and the target transgenes are in the other parent, and the parents exhibit no transgenic phenotype. In other embodiments, all the hemizygous transgenes may be present in a single parent, as long as they do not impart sterility or lethality. This approach is desirable when transformation of one parent is comparatively easy, so that introgression of transgenes into a parent of a different genetic background is not necessary.

Phenotyping

Populations of progeny plants can be screened and/or selected for those members of the population that have a trait or phenotype, or a combination of traits or phenotypes conferred by the particular combinations of transgenes. Phenotyping can be performed in a greenhouse and/or laboratory and/or in the field. In some embodiments, a population of plants can be selected that has improved heterosis, grain yield, tolerance to abiotic stress such as drought stress, osmotic stress, or nitrogen deficiency, soil aluminum, cold stress, frost stress, density stress, heat stress, oxidative stress, low light tolerance, herbicide stress, as well as improved water use efficiency, nitrogen use efficiency, phosphate use efficiency, seed oil or protein content, lignin content, biotic or pest resistance, biomass, chemical composition, plant architecture, flowering time, and/or biofuel conversion properties. In some cases, selection and/or screening can be carried out over multiple transformation events. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. But, in many cases a phenotypic measure is yield of harvestable material under typical field cultivation conditions, i.e. without an intentionally applied selection pressure. Selection and/or screening can be carried out to choose those transgenic plants having a statistically significant difference in yield (e.g., grain, vegetative biomass, or stem sucrose yield) relative to a control plant that lacks the combination of transgene. Selection and/or screening can be carried out to choose those transgenic plants having a statistically significant difference in an abiotic stress tolerance level relative to a control plant that lacks the transgene. While the focus is most often on individuals with stacks exhibiting improved performance, it is sometimes useful to identify stacks of significantly impaired performance over a control. Identification of undesirable transgene stacks can be useful in designing subsequent improvement rounds so as to eliminate or minimize their occurrence.

To test for density stress tolerance, the testing population can be planted at an excessive density for the respective genetic background controls, and yield of individual plants scored for identifying the best performing individuals (see, for example, Mansfield and Humm, 2014, *Crop Science*, 57:157-173).

A heterotic group comprises a set of genotypes that perform well when crossed with genotypes from a different heterotic group. Inbred lines are classified into heterotic groups, and are further subdivided into families within a heterotic group, based on several criteria such as pedigree, molecular marker-based associations, and performance in hybrid combinations (see e.g. Smith at al. (1990) Theor. Appl. Gen. 80:833-840). For example for corn, the two most widely used heterotic groups in the United States are referred to as "Iowa Stiff Stalk Synthetic" (BSSS) and "Lancaster" or "Lancaster Sure Crop" (sometimes referred to as NSS, or iron-Stiff Stalk).

To test for nitrogen use efficiency, seeds of a testing population can be planted in a field using standard agronomic practices for the region, along with non-transgenic controls of the same genetic background. Fertilizer is applied at about 50% of the optimal level for the respective location, so that yield of non-transgenic plants is negatively impacted. See, Example 3.

Aside from pre-defined phenotypical observations to be made on testing populations such as those appropriate to screen for stress tolerances, the appearance of nearby planted negative controls can be useful in comparing to individuals in the transgenic population for observation of phenotypic differences that may be caused by some transgenic combinations. Non-limiting examples of traits to be observed include ear diameter, ear height, ear leaf length, ear leaf weight, ear length, ear position, ear number, grain color, kernel length, kernel number, kernel row arrangement, kernel row number, kernel type, kernel width, leaf length, leaf width, tassel size, tassel type, and uppermost ear shape, and others traits described, for example, in the Maize Traits for Fieldbooks. See the world wide web at "cril.cimmyt.org/confluence/display/MBP/Activity+2.1.2+-+Maize+Traits+for+Fieldbooks."

The methods provided can be used to generate a very large number of different combinations of promoters operably linked to sequences to be expressed. But very large numbers can also have drawbacks, so in designing combinations it is often desirable to limit the number of combinations. A limit is imposed by the need to replicate individual genotypes so to understand the statistical significance of the phenotypes observed, and as such this limit is correlated with the size of any designed study. But, a limited "unit" of related variability is also helpful in side-by-side comparisons. For example, four coding sequences and four promoters can be combined in 225 non-null ways. Planting a population with having no more than this variability on a contiguous and identifiable plot helps by minimizing the environmental variability exposure and allowing for manageable comparative phenotyping. In other words, when related genotypes are replicated in a defined area, individuals can be readily examined for visually noticeable differences. As such, it is desirable to design variability units that occupy generally no more than about half a hectare or about one acre. For example, 225 corn genotypes replicated 10-fold, i.e. about 2250 plants, are typically planted on about one tenth of an acre. Hence, for example, for testing five promoters and six coding sequences, the five promoters can be used in making five parents with all combinations of the five promoters taken by four, and the six coding sequences can be used in making fifteen parents with all the combinations of the six coding sequences taken by four. The seventy-five crosses of the five promoter parents to the fifteen coding sequence parents generate seventy-five units, which can be grown in the field on about seven and a half acres.

When seeking to first sort through the candidate expressed sequences and their optimal expression patterns, it is preferable to make and phenotype a population of plants of a uniform genetic background if possible. However, a reduced number of candidates can be tested in variable genetic backgrounds. When the tested populations are sufficiently large, the interaction of different stack combinations with known QTLs can thus be determined. Consequently, the methods provided herein can be used in conjunction with traditional breeding selections to produce cultivars with improved traits.

Genotyping

As described herein, plants that are identified as having an improved phenotypic feature can be genotyped using any methodology. Genotype refers to the combination of transgenes, i.e. activator and target transgenes, present in an individual plant, which can be determined by a variety of methods known in the art, such as PCR with transgene-specific primers or Southern blotting. Genotype can also refer to the combination of alleles that determines a characteristic or trait, and it can be indirectly characterized using markers or directly characterized by nucleic acid sequencing. Suitable markers include a genetic marker, or some other type of marker. The genotype can reflect the sequence of a portion of a chromosome, an entire chromosome, a portion of the genome, or of the entire genome. In some embodiments, leaf punches from individuals either to be selected for testing or identified as having an improved phenotypic feature can be genotyped. In some embodiments, seed chipping, in which the genetics of the seed can be assessed without destroying the seed, is used to select a subset of individuals from the progeny population. See, for example U.S. Pat. No. 7,502,113. Accordingly, a population can be created that mixes a large number of transgenes, for example activator and target transgene components. Subsequently, as it may become desirable if informed by new performance data, a subpopulation comprising only a defined subset of transgenes and corresponding activators can be selected and studied. Or similarly, individuals from a large population can be eliminated from a study by genotyping plants before planting if they are deemed to contain component combinations that are undesirable, such as activator transgenes with identical polypeptides driven by promoters of overlapping tissue specificities.

Improvement Rounds

Once a stack of transgenes is identified by any means as having a desirable phenotypic performance, the stack can be subjected to additional rounds of improvement by adapting the methods used to identify the combination. In one type of improvement, the desired transgenes are maintained in the background of all the plants of a testing population, and additional transgene combinations are also stacked.

In a second type of improvement, expression of a defined stack of sequences is driven by different combinations of promoters, to identify optimal promoters capable of further improving the stack phenotype. This approach can be especially useful in fine-tuning or optimizing a desirable phenotype to a different genetic background, such as an elite inbred variety or hybrid that is different from others previously characterized.

It will be appreciated that the two improvement methods are not mutually exclusive, and they can be combined in a single testing population.

When identified using of a two-component system, direct fusion transgene constructs can be made using the activator transgene promoters and/or other promoters of similar expression patterns, upstream and operably linked to the respective target sequences of interest. The direct fusion constructs can be transformed and used in improvement rounds or in generating commercial transgenic events.

In some embodiments, improvements may be made using the top performing materials from a phenotyped population. For example, the best individuals can be crossed to each other and their progeny phenotyped. When the diversity of original transgenes is large, this approach may more quickly result in recognition of improved stacks. This approach works well when the testing population is made up of inbred lines or uniform true breeding populations. When the testing population is made up of hybrid plants, it is possible to make one or more corresponding populations by crosses to isogenic parents so as to cause similar transgene segregation as in the hybrid testing population. By first genotyping the top performers of the testing population The improvement rounds can be cycled as many times as needed to develop transgene stacks of incrementally enhanced performance in the respective assays or field conditions.

The invention will be further described in the following examples, which do not limit the scope of the invention described in the claims.

EXAMPLES

Example 1

Expression Constructs

This example illustrates constructs that can be used for making transgenic plants expressing combinations of transgenes. For direct fusion expression constructs, a plant promoter is operably linked to the sequence to be transcribed (FIG. 1A). A transgenic plant harboring the construct will express the sequence according to the tissue expression pattern of the respective plant promoter.

For a two component system, at least two constructs are required, one for the target transgene and one for the activator transgene (FIG. 1B). An activator transgene expresses an activation polypeptide made up of a DNA binding domain fused to a transcription activation domain. A target transgene has an upstream activating sequence (UAS), which is specifically recognized by the DNA binding domain of the activation polypeptide, upstream of a minimal plant promoter and a target sequence. When present in the same cell, the activation polypeptide binds to the UAS, and the target sequence is transcribed. In the absence of an activation polypeptide, the target transgene does not express the target sequence and thus causes no transgenic phenotype. More than one activator and more than one target transgene may be stacked in the same parental line. When a parental line with an activator transgene is crossed with a parental line with a matching target transgene, i.e., the DNA binding domain of the activator can bind the UAS of the target, the hybrid will express the target sequence and therefore exhibit the phenotype conferred by the target sequence expression.

Example 2

Producing Transgenic Plants

This example illustrates the transformation of corn and production of corn plants that can be used as parent organisms. It will be appreciated that similar methods can be applied to other plants. Corn is subjected to *Agrobacterium*-mediated transformation using T-DNA constructs with activation or target constructs cloned between left and right borders. Transformation is performed according to established protocols (see, for example, U.S. Pat. No. 7,939,328). Successful transformation and the number of inserted transgenes is confirmed by Southern blotting. The homozygous or hemizygous state can be determined by quantitative PCR. Once a transformation event is selected for advancement, the genomic sequence flanking the insert is determined, and PCR primers are designed based on genomic and insert sequences; then homozygous or hemizygous state of specific samples can be determined by PCR.

For the two component system, the expression of activator polypeptides is confirmed to occur as expected for the promoter of the respective activator transgene by crossing the transformed activator plant to a plant having an target transgene with an UAS matching the DNA binding domain of the activator transgene. The expected expression of the target transgene is verified by quantitative RT-PCR (qRT-PCR), Northern blots, Western blots, and ELISA. Suitable activator transgenes are introgressed into an inbred line, such as Mo17 for corn. For most applications, the transgene is brought to a homozygous state by selfing, followed by molecular and/or genetic characterization of the candidate parental plants.

Regenerated plants having target transgenes are tested for target transgene expression by RT-PCR to ensure expression is not caused by positional effects of transgene insertion. Then, candidate transgenic events are crossed to activator lines, and expression of the target sequence in the progeny is verified by RT-PCR, Northern blots, Western blots, and ELISA. Suitable target transgenes are introgressed into a B line, for which an isogenic A line with cytoplasmic male sterility (CMS) exists. The transgene is brought to a homozygous state by selfing followed by molecular and/or genetic characterization of the starting parental plants.

Example 3

Phenotyping of Testing Populations

This example illustrates how testing populations (e.g., corn populations) expressing various combinations of transgene are evaluated. It will be appreciated that similar methods can be adapted for other plants. For nitrogen use efficiency (NUE), seeds of a corn testing population are mixed and planted in a field using standard agronomic practices for the region, along with non-transgenic controls of the same genetic background. Fertilizer is applied at about 50% of the optimal level for the respective location, so that yield of non-transgenic plants is negatively impacted. For example, at a location where the most profitable application rate is 150 lb/acre, the application rate for NUE phenotyping of the test population is 75 lb/acre.

Ears of plants are harvested, and categorized into appropriate groups for the study, such as negative controls, random transgenic field samples, or bulk transgenic population. One phenotype measurement is ear weight. For selected samples, such as a group identified as top performers by ear weight, grain weight yield per ear is also measured and recorded.

Negative control plants are planted in identifiable rows for easy reference relative to the testing population in regards to additional phenotypes of interest. The phenotypes noted below are examined for the control and testing population, either in the field or on and any observed significant differences are noted and quantified, and the individuals of the transgenic testing populations exhibiting the differences are genotyped. The phenotypes examined in the field are ear diameter, ear height, ear leaf length, ear leaf weight, ear length, ear position, grain color, kernel length, kernel number, kernel row arrangement, kernel row number, kernel type, kernel width, leaf length, leaf width, tassel size, tassel type, and uppermost ear shape.

To select for drought resistance, the seeds of a corn testing population are mixed and planted in a field using standard agronomic practices for that region, along with non-transgenic controls of the same genetic background. The entire field is grown under deficit irrigation for the respective season, such that the controls exhibit leaf rolling to a scorable degree for a substantial part of the growing season. A first phenotypic pass through the transgenic testing population in the field visually identifies the least chlorotic and least stunted individuals. This group is designated as top performers, and its grain weight yield per ear is also measured and recorded, along with similar measurements for controls.

Kernels can be screened for oil content using methods such as those described in U.S. Publication No. 20100024070A1. For example, the seeds of a corn testing population and similarly grown non-transgenic controls are harvested. An analytical method based on Fourier transform near-infrared (FT-NIR) spectroscopy is developed, validated, and used to perform a high-throughput screen of transgenic kernels for alterations in kernel oil content. To calibrate the FT-NIR spectroscopy method, a subpopulation of transgenic kernels is randomly selected and analyzed for oil content using a direct primary method. Fatty acid methyl ester (FAME) analysis by gas chromatography-mass spectroscopy (GC-MS) is used as the direct primary method to determine the total fatty acid content for each kernel and produce the FT-NIR spectroscopy calibration curves for oil.

To analyze kernel oil content using GC-MS, seed tissue is homogenized in liquid nitrogen using a mortar and pestle to create a powder. The tissue is weighed, and 5.0±0.25 mg are transferred into a 2 mL Eppendorf tube. The exact weight of each sample is recorded. One mL of 2.5% $H_2SO_4$ (v/v in methanol) and 20 µL of undecanoic acid internal standard (1 mg/mL in hexane) are added to the weighed seed tissue. The tubes are incubated for two hours at 90° C. in a pre-equilibrated heating block. The samples are removed from the heating block and allowed to cool to room temperature. The contents of each Eppendorf tube are poured into a 15 mL polypropylene conical tube, and 1.5 ml, of a 0.9% NaCl solution and 0.75 mL of hexane are added to each tube. The tubes are vortexed for 30 seconds and incubated at room temperature for 15 minutes. The samples are then centrifuged at 4,000 rpm for 5 minutes using a bench top centrifuge. If emulsions remain, then the centrifugation step is repeated until they are dissipated. One hundred µL of the hexane (top) layer is pipetted into a 1.5 mL autosampler vial with minimum volume insert. The samples are stored no longer than 1 week at −80° C. until they are analyzed.

Samples are analyzed using a Shimadzu QP-2010 GC-MS (Shimadzu Scientific Instruments, Columbia, Md.). The first and the last samples of each batch consist of a blank (hexane). Every fifth sample in the batch also consists of a blank. Prior to sample analysis, a 7-point calibration curve is generated using the Supelco 37 component FAME mix (0.00004 mg/mL to 0.2 mg/mL). The injection volume is 1 µL. The GC parameters are as follows: column oven temperature: 70° C., inject temperature: 230° C., inject mode: split, flow control mode: linear velocity, column flow: 1.0 mL/min, pressure: 53.5 mL/min, total flow: 29.0 mL/min, purge flow: 3.0 mL/min, split ratio: 25.0. The temperature gradient is as follows: 70° C. for 5 minutes, increasing to 350° C. at a rate of 5 degrees per minute, and then held at 350° C. for 1 minute. The MS parameters are as follows: ion source temperature: 200° C., interface temperature: 240° C., solvent cut time: 2 minutes, detector gain mode: relative, detector gain: 0.6 kV, threshold: 1000, group: 1, start time: 3 minutes, end time: 62 minutes, ACQ mode: scan, interval: 0.5 second, scan speed: 666, start M/z: 40, end M/z: 350. The instrument is tuned each time the column is cut or a new column is used.

The data are analyzed using the Shimadzu GC-MS Solutions software. Peak areas are integrated and exported to an Excel spreadsheet. Fatty acid peak areas are normalized to the internal standard, the amount of tissue weighed, and the slope of the corresponding calibration curve generated using the FAME mixture. Peak areas are also multiplied by the volume of hexane (0.75 mL) used to extract the fatty acids.

The same kernels that are analyzed using GC-MS also are first analyzed by FT-NIR spectroscopy, and the oil values determined by the GC-MS primary method are entered into the FT-NIR chemometrics software (Bruker Optics, Billerica, Mass.) to create a calibration curve for oil content. The actual oil content of each kernel analyzed using GC-MS is plotted on the x-axis of the calibration curve. The y-axis of the calibration curve represents the predicted values based on the best-fit line. Data points are continually added to the calibration curve data set.

Kernels from the testing population are analyzed by FT-NIR spectroscopy. Sarstedt tubes containing kernels are placed directly on the lamp, and spectra are acquired through the bottom of the tube. The spectra are analyzed to determine kernel oil content using the FT-NIR chemometrics software (Bruker Optics) and the oil calibration curve. Results for experimental samples are compared to population means and standard deviations calculated for transgenic kernels from similarly grown plants. Each data point is assigned a z-score ($z=(x-mean)/std$), and a p-value is calculated for the z-score.

Transgenic kernels with oil levels that differ by more than two standard deviations from the population mean are genotyped.

Example 4

Producing Plants Biased Towards Combinations of 2-4 Transgenes Using Direct Fusion Constructs Eight transgenes, A-H, are chosen as likely to affect NUE when overexpressed. Eight transgenic corn plants are made, each bearing a single transgene from the A-H group expressed under control of an appropriate plant promoter. Transgens A-D are introgressed into the Mol7 genetic background, and transgenes E-H are introgressed into a B73 genetic background. It will be appreciated that other combinations of parental pairs also could be used. The plants selected for testing have unlinked single transgenic insertions.

Four plants homozygous for the following pairs are made: AB, CD, EF, and GH. The four plants are crossed to non-transgenic plants of their corresponding genetic background to make hemizygous parents. A male parent is made by crossing the homozygous AB to the homozygous CD to obtain a hemizygous ABCD (Mol7) parent. A female parent is made by crossing the homozygous EF to the homozygous GH plants, selfing the $F_1$ hybrid, and selecting from the progeny a homozygous EFGH plant; the hemizygous parent is then made by crossing the homozygous EFGH with an A73 plant (A73 refer to the CMS but otherwise isogenic versions of B73).

Seeds for testing are of $F_1$ hybrids made by the following crosses, all based on hemizygous parents.
  ABCD (Mol7) x EF (A73)
  ABCD (Mol7) x GH (A73)
  AB (Mol7) x EFGH (A73)
  CD (Mol7) x EFGH (A73)
  ABCD (Mol7) x EFGH (A73)

About 300 seeds are collected from each of the top four crosses and 800 from the last one to make up the testing population.

Example 5

Producing Plants Biased Towards Combinations of 2-4 Transgenes Using Direct Fusion Constructs Alternatively, the testing population can be created to have a higher representation of 2-4 transgene combinations of the transgenes unpaired in either the male or female parents; for example, it has a uniform representation of the A-C transgene pair. The same eight transgenic plants described in Example 4 can be used as the starting material. Eight plants homozygous (H) for the following pairs are made: AB, CD, AC, BD, in the Mol7 background, and EF, GH, EG, and FH in the B73 background. The eight plants are crossed to non-transgenic plants of their corresponding genetic background to make hemizygous parents. Quadruple hemizygous parents are also made as in Example 4.

Seeds for testing are made by the following crosses of hemizygous parents:
  ABCD x EF
  ABCD x GH
  ABCD x EG
  ABCD x FH
  AB x EFGH
  CD x EFGH
  AC x EFGH
  BD x EFGH About 300 seeds from each cross are collected and pooled to make up the testing population.

Example 6

Producing Plants Having Combinations of Transgenes Using a Two-Component System

In this example, eight candidate transgenes are tested for their ability to impart a significantly improved NUE phenotype when overexpressed in specific stacks. Expression of each candidate transgene is driven by either one of two different promoters.

Production of Female Parents with Target Transgenes

The eight sequences to be expressed, designated A through H, are subcloned into the following twelve target vectors, in which h, g, l, and p represent respectively UASs specific to Hap1, Gal4, Leu3, and Ppr1:
  hA, hB, gB;
  gC, gD, lD;
  lE, lF, pF;
  pG, pH, and hH.

Each construct is transformed into corn. Through repeated crossing and parent and progeny genotyping, two corn B lines are generated in the B73 background having the following homozygous target transgene combinations:
  (i) hA, hB, gC, gD, lE, lF, pG, and pH; and
  (ii) hA, gB, gC, lD, lE, pF, pG, and hH.

Independent segregation of transgenes is verified.

The homozygous B lines are crossed to isogenic CMS A lines to produce females that are hemizygous for the eight respective target transgenes. The two hemizygous females are crossed with the activator males described below.

Production of Male Parents with Activator Transgenes

Two promoters are used at this stage: root preferential promoter pR, and ubiquitously expressing promoter pU. These promoters are subcloned in the following eight activation vectors:
  pR-Hap1, pU-Hap1,
  pR-Gal4, pU-Gal4,
  pR-Leu3, pU-Leu3,
  pR-Ppr1, and pU-Ppr1.

Each construct is transformed into corn to generate eight transformation events, which are then introgressed into Mol7. Through repeated crossing and genotyping, sixteen corn R lines are generated, having the following homozygous activator transgene combinations:

1. pR-Hap1, pR-Gal4, pR-Leu3, pR-Ppr1;
2. pU-Hap1, pR-Gal4, pR-Leu3, pR-Ppr1;
3. pR-Hap1, pU-Gal4, pR-Leu3, pR-Ppr1;
4. pR-Hap1, pR-Gal4, pU-Leu3, pR-Ppr1;
5. pR-Hap1, pR-Gal4, pR-Leu3, pU-Ppr1;
6. pR-Hap1, pR-Gal4, pU-Leu3, pU-Ppr1;
7. pU-Hap1, pR-Gal4, pR-Leu3, pU-Ppr1;
8. pR-Hap1, pU-Gal4, pR-Leu3, pU-Ppr1;
9. pR-Hap1, pU-Gal4, pR-Leu3, pU-Ppr1;
10. pU-Hap1, pR-Gal4, pU-Leu3, pR-Ppr1;
11. pR-Hap1, pU-Gal4, pU-Leu3, pR-Ppr1;
12. pR-Hap1, pU-Gal4, pU-Leu3, pU-Ppr1;
13. pU-Hap1, pR-Gal4, pU-Leu3, pU-Ppr1;
14. pU-Hap1, pU-Gal4, pR-Leu3, pU-Ppr1;
15. pU-Hap1, pU-Gal4, pU-Leu3, pR-Ppr1;
16. pU-Hap1, pU-Gal4, pU-Leu3, pU-Ppr1.

Independent segregation of transgenes is verified.

The homozygous lines are crossed to isogenic non-transgenic Mo17 restorer lines to produce males that are hemizygous for the four respective activator transgenes. These sixteen types of hemizygous activator males are crossed with the two hemizygous target females made described above.

Production of Seeds for Performance Testing

About 50 of each of the two hemizygous females produced above are planted in a honeycomb pattern with the sixteen males produced above, such that the female ears are similarly exposed to all shedding male pollen. Each of the parent plants generate either 256 ($2^8$) distinct female or 16 ($2^4$) distinct male gamete transgene genotypes, as their genetic makeup can be visualized with Prunnett squares. Accordingly, the two females and 16 males can give rise to plants with 131,072 (2×256×16×16) hybrid genotypes or genetic combinations. When grown, the resulting hybrids will express different subsets of the eight target transgenes in different combinations and with their expression pattern dictated by either of the two activation line promoters.

For example, a plant resulting from crossing a gamete of genotype hA, gC, gD, pH with a gamete of genotype pU-Hap1, pR-Leu3, pU-Ppr1 will overexpress transgenes A and H, with expression of both driven by promoter pU.

The seeds of female ears are harvested at maturity for performance testing.

Performance Testing

Two populations of about 10,000 hybrids are planted in the field at different locations, and phenotyped as described in Example 3. Fifty (50) non-transgenic hybrids of the same parental genetic background are planted and marked in the same field as readily identifiable negative controls. Plants are allowed to grow to maturity, and then ears are harvested, keeping the ears of the negative controls separate from those from the rest of the field.

The entire population of negative controls is phenotyped. A random sample of approximately 250 ears, i.e. 2.5%, of each of the stacked transgenic plant populations, is also phenotyped. Then, the ears of entire stacked transgenic populations are sorted so as to isolate the top 2% performing samples, as described in Example 3. These top perfomers are genotyped from the cob or pericarp maternal tissue.

Data collected from the performance testing is used in analysis of variance (ANOVA) to identify combinations of transgenes with significantly improved yield performance. The statistical significance of the different stack and promoter combinations at the frequencies found in the top performing individuals is tested against the known genotypic structure of the testing population.

Example 7

Further Improvements in Performance of Plants Having Combinations of Transgenes Using a Two-Component System by Promoter Optimization In this example, further improvement of performance of a specific transgene combination identified as in Example 6 can be performed using promoter optimization. This example is based on improving a combination of overexpression of both transgenes A and B driven by the root promoter pR with overexpression of transgene D driven by the ubiquitous promoter pU.

Female Parents

Using the transgene designations as in Example 6, the female parent is made as a B line homozygous for transgenes hA, gB, and lD. Selfing of the females in crossing to the male parents is prevented by de-tasseling.

Male Parents

Four plant promoters with limited tissue expression specificity, i.e. none exhibiting ubiquitous expression, are chosen for this example: pR expressing in the roots, pV expressing in vascular tissue, pG expressing in photosynthetic (green) tissue, and pS expressing in seeds. Each of these four promoters is placed in activation vectors having Hap1, Gal4, and Leu3 domains. Two homozygous plants are made with the following transgenes:

1. pR-Hap1, pV-Hap1, pR-Gal4, pV-Gal4, pR-Leu3, pV-Leu3;
2. pG-Hap1, pS-Hap1, pG-Gal4, pS-Gal4, pG-Leu3, pS-Leu3.

The male parent is made by crossing the two lines above. The resulting twelve hemizygous activator transgenes will then segregate in crossing to the female parents described above to generate a testing population.

Alternatively, male parents can be generated that resulting in a testing population biased towards plants expressing transgenes driven by fewer multi-promoter activators. Four homozygous plants are made with the following transgenes:

3. pR-Hap1, pR-Gal4, pR-Leu3;
4. pV-Hap1, pV-Gal4, pV-Leu3;
5. pG-Hap1, pG-Gal4, pG-Leu3;
6. pS-Hap1, pS-Gal4, pS-Leu3.

Four different hemizygous male parents are made: two by crossing each of the homozygous plants 3 and 4 to the homozygous plant 2 described above in this section, and another two by crossing each of the homozygous plants 5 and 6 to the homozygous plant 1 described above in this section. The female and male parents can be crossed as described in Example 6 and performance tested.

Example 8

Further Improvements in Performance of Plants Having Combinations of Transgenes Using a Two-Component System by Adding Transgenes In this example, performance of a specific transgene stack identified as in Example 6 is improved by expressing additional transgenes. This example is based on improving overexpression of both transgenes A and B driven by the root promoter pR with overexpression of transgene D driven by the ubiquitous promoter pU. Transgenes J, K, L, and M are tested, driven again by either pR or pU, and stacked to A/B/D.

Female Parents

Two plants are made, both homozygous for hA, hB, and gD, and either hemizygous for (i) lJ, lK, pL, and pM; or (ii) lJ, pK, lL, and pM. The detasseled B line females (or an A line with CMS) are crossed to the male parents described below to make the testing population.

Male Parents

Two male parents are made, both homozygous for pR-Hap1 and pU-Gal4, and either hemizygous for (i) pR-Leu3, and pU-Ppr1; or (ii) pU-Leu3, and pR-Ppr1. Both of these parents are used as pollinators for the female parent described in this example. The female and male parents can be crossed as described in Example 6 and performance tested.

Figure 2:
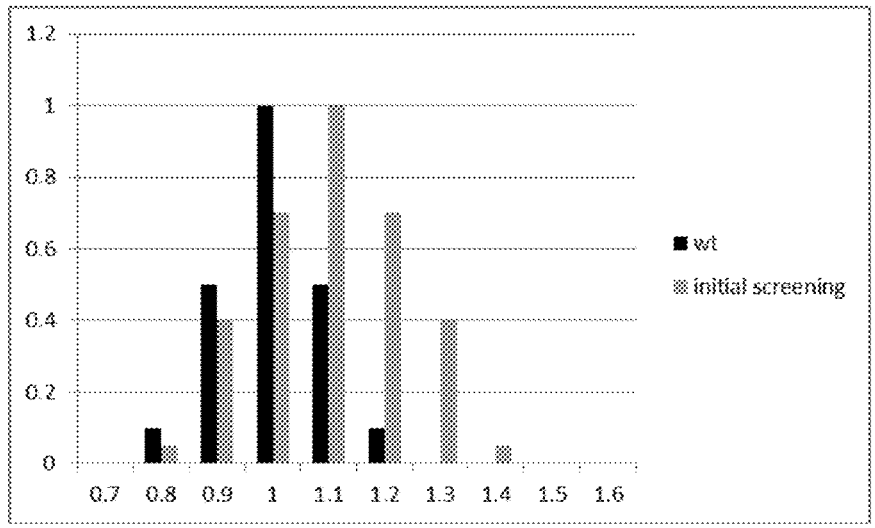
FIG. 2A is a bar graph of a normalized distribution of grain yield per plant that can be obtained for wild type and a first generation testing population of combined stacks. Top performers are selected for use in the improvement round.
FIG. 2B is a bar graph of a normalized distribution of grain yield per plant that can be obtained for wild type and an improvement testing population. The improvement population is based on promoter optimization of a selected transgene combination identified by the initial screen.
Figure 2:
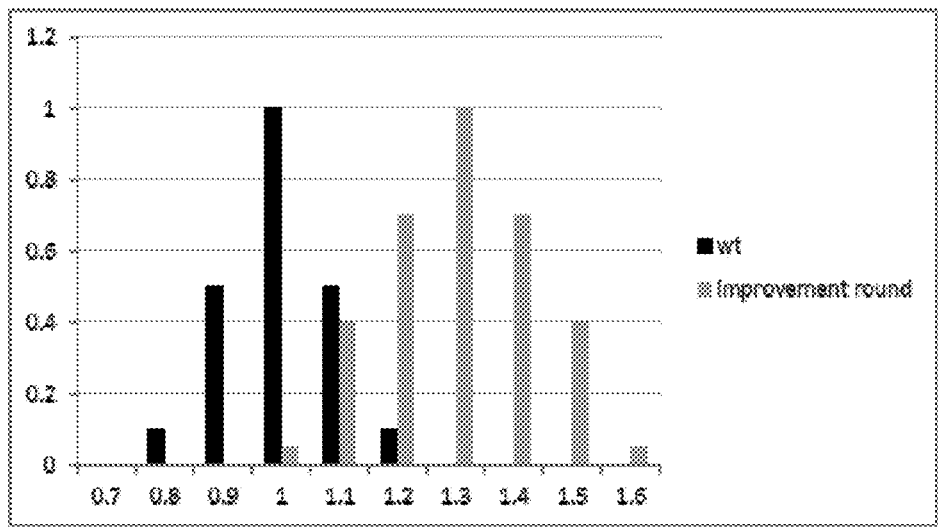

FIGS. 2A and 2B illustrate results that can be obtained with stack testing and improvement. Once a combination of coding sequences and promoters is identified that achieves a commercially acceptable performance, the respective transgene combination is made in a direct fusion construct and transgenic plants of the expected phenotype are made.

Example 9

Design of a Population of Two Component Hybrids for Stacks Combining Transgenes with Restricted Tissue Expression In this example, a population is made for testing four different promoters with restricted expression patterns in driving four transgenic sequences in all possible combinations in corn.

Female Parents

B73 lines are made homozygous for four independently segregating target transgenes: hA, hB, hC, and hD. "h" designates the UAS of Hap1. The females are hemizygous A73 plants made by crossing wild type A73 with the homozygous B73 lines.

Male Parents

Mol7 lines are made homozygous for four activator transgenes, all driving expression of an activator polypeptide with a Hap1 DNA binding domain. The four activator transgenes are pID-Hap1, pS-Hap1, pV-Hap1, and pG-Hap1. The promoters of these transgenes, pRID, pS, pV, and pG drive transcription respectively as follows: in root induced by drought, in seed, in vascular tissue, and in photosynthetic tissue. The males used to produce the hybrid population are hemizygous, made by crossing the homozygous line to wild type Mol7.

The Hybrid Testing Population

A hybrid population is made by crossing the hemizygous females described in this Example with the hemizygous males described in this Example, and phenotyped as described in Example 6.

Example 10

Generation of a Testing Population with Transgene Expression Combinations

In this example, the phenotype first noticed with transgenes A, B, and D is improved by testing the combined expression of these transgenes under control of four different promoters P1-P4.

Female Parents

A plant is made homozygous for hA, gB, and lD.

Population of Male Parents

Three precursor allelic transgenes are made and transformed, each having four expression cassettes:
P1-Hap1, P2-Hap1, P3-Hap1, and P4-Hap1;
P1-Gal4, P2-Gal4, P3-Gal4, and P4-Gal4; and
P1-Leu3, P2-Leu3, P3-Leu3, and P4-Leu3.

Each expression cassette is flanked by specific zinc finger nuclease recognition domains nrd1-nrd4. For example, the first transgene comprises in 5' to 3' order the following elements: nrd1-P1-Hap1-nrd1-nrd2-P2-Hap1-nrd2-nrd3-P3-Hap1-nrd3-nrd4-P4-Hap1-nrd4.

Four additional plants are made for processing the precursor allelic transgenes such that selective portions of the transgenes can be deleted. Each of the four plants express a zinc finger nuclease, ZN1, ZN2, ZN3, or ZN4, where each nuclease is capable of recognizing and cleaving a nuclease recognition domain. For example, ZN1 is capable of recognizing and cleaving nrd1, ZN2 is capable of recognizing and cleaving nrd2, and so forth. Expression cassettes of the precursor allelic transgenes are then processed by selective deletion through crosses to plants expressing zinc finger nucleases, followed by selection of progeny with partial deletions of the precursor inserts. Plants so generated are made homozygous for the following unlinked transgenes, and they are progenitors of the population of male parents.

(1) P1-Hap1, P1-Gal4, P1-Leu3
(2) P2-Hap1, P2-Gal4, P2-Leu3
(3) P3-Hap1, P3-Gal4, P3-Leu3
(4) P4-Hap1, P4-Gal4, P4-Leu3

An intermediate set of progenitors is made by crossing plants (1) through (4) to each other, to form all combinations of essentially allelic heterozygotes. Finally, the population of male parents is made by open pollinating the intermediate set of progenitors, thus generating a population capable of producing pollen combining all the four alleles at all the three transgenic insertion loci.

This population of male parents is grown in proximity to the female parents, so that pollen from each male parent is randomly likely to fertilize female flowers to produce the testing population.

Example 11

Generation of a Testing Population by Genotyping

This example illustrates creating a testing population by selecting a subset of individuals to be tested from a more diverse population of seeds with various combinations of transgenes. A testing population of corn seeds combining multiple transgenes is made.

The testing population is made according to Example 6. Seeds of the testing populations are germinated and grown to seedling stage in the green house. The seedlings are genotyped. Seedlings comprising transgenes pH and hH are discarded. The remaining seedlings are transferred to the field for performance testing.

Example 12

Improvement by Crossing of Best Performing Individuals

Parental plants of a first testing population are made similarly as described in Example 6, but with the difference that both the male and female hemizygous parents are in the same isogenic genetic background. Consequently, the male and female designation is arbitrary as either parent could serve as female by detasseling. For phenotyping, the testing populations are grown out under deficit irrigation such that at flowering, control plants suffer from clearly visible signs of drought such as wilting and chlorosis. The top about 1% performers of the population are identified as the plants with the least severe drought symptoms. When mature, they are manually cross pollinated. Their seeds are harvested and form the second testing population. The top performers are genotyped.

The second testing population is grown and phenotyped similarly to the first testing population. The top performers are identified and cross-pollinated to form a subsequent testing population. The top performers are genotyped.

The planting, phenotyping, selection, genotyping, and crossing of top performing individuals can be repeated in a number of subsequent testing populations to find combined transgene stacks with further performance improvements.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying a combination of genetic elements responsible for a desirable phenotype of a plant, wherein said method comprises:
   (a) selecting at least four target transgenes, wherein each target transgene of said at least four target transgenes comprises a regulatory region comprising an upstream activating sequence operably linked to a nucleotide sequence to be expressed, whereby said upstream activating sequence of each of said at least four target transgenes is the same or different;
   (b) selecting at least two activator transgenes, wherein each activator transgene comprises a plant promoter operably linked to a sequence encoding a chimeric polypeptide comprising a DNA binding domain fused to a transcription activation domain, wherein each DNA binding domain of said at least two chimeric polypeptides binds to the upstream activating sequence comprised within said regulatory region of at least one of said at least four target transgenes;
   (c) obtaining a first parental plant and a second parental plant, wherein each of said at least four target transgenes and said at least two activator transgenes (i) is individually present in either said first parental plant or said second parental plant, (ii) is unlinked from each of the other of said at least four target transgenes and said at least two activator transgenes that are present within the same said first parental plant or said second parental plant, and (iii) is in a hemizygous state within said first parental plant or said second parental plant;
   (d) sexually crossing said first parental plant and said second parental plant to produce a population of progeny plants, whereby said population of progeny plants has different combinations of said at least four target transgenes and said at least two activator transgenes;
   (e) comparing different plants of said population of progeny plants to one another and selecting at least one progeny plant from said population as having said desirable phenotype to obtain a selected progeny plant; and
   (f) determining which target transgenes and activator transgenes are present within said selected progeny plant, thereby identifying a combination of genetic elements responsible for said desirable phenotype of a plant.

2. The method of claim 1, wherein at least one of said nucleotide sequences to be expressed is a nucleotide sequence encoding a dominant negative polypeptide.

3. The method of claim 1, wherein said first parental plant comprises said at least four target transgenes, and said second parental plant comprises said at least two activator transgenes.

4. The method of claim 1, wherein said chimeric polypeptide encoded by each of said at least two activator transgenes is the same.

5. The method of claim 1, wherein said upstream activating sequence of each of said at least four target transgenes is the same.

6. The method of claim 1, wherein said plant promoter of each of said at least two activator transgenes is different.

7. The method of claim 1, wherein said method further comprises, after said step (f):
   (a1) selecting at least four target transgenes, wherein each target transgene of said at least four target transgenes comprises a regulatory region comprising an upstream activating sequence operably linked to a nucleotide sequence to be expressed, and wherein said selected at least four target transgenes includes said target transgenes determined to be present within said selected progeny plant in step (f), and whereby said upstream activating sequence of each of said at least four target trans genes is the same or different;
   (b1) selecting at least two activator transgenes, wherein each activator transgene comprises a plant promoter operably linked to a sequence encoding a chimeric polypeptide comprising a DNA binding domain fused to a transcription activation domain, wherein each DNA binding domain of said at least two chimeric polypeptides binds to the upstream activating sequence comprised within said regulatory region of at least one of said at least four target transgenes, and wherein said selected at least two activator transgenes includes said activator transgenes determined to be present within said selected progeny plant in step (f);
   (c1) obtaining a third parental plant and a fourth parental plant, wherein each of said at least four target transgenes of said step (a1) and said at least two activator transgenes of said step (b1) (i) individually present in either said third parental plant or said fourth parental plant, (ii) is unlinked from each of the other of said at least four target trans genes and said at least two activator trans genes that are present within the same said third parental plant or said fourth parental plant, and (iii) is in a hemizygous state within said third parental plant or said fourth parental plant;
   (d1) sexually crossing said third parental plant and said fourth parental plant to produce a second population of progeny plants, whereby said second population of progeny plants has different combinations of said at least four target transgenes of step (a1) and said at least two activator transgenes of step (b1);
   (e1) comparing different plants of said second population of progeny plants to one another and selecting at least one progeny plant from said second population as having a desirable phenotype to obtain a second selected progeny plant; and
   (f1) determining which target transgenes and activator transgenes are present within said second selected progeny plant, thereby identifying a combination of genetic elements responsible for a desirable phenotype of a plant.

8. The method of claim 1, wherein said first parental plant and said second parental plant are selected from the group consisting of *Zea mays*, *Sorghum bicolor*, *Triticum aestivum*, and *Oryza sativa*.

9. The method of claim 1, wherein said first parental plant or said second parental plant is cytoplasmically male sterile.

10. The method of claim 1, wherein said selecting of step (e) is based at least in part on results under field testing conditions.

11. The method of claim 1, wherein said first parental plant and said second parental plant belong to distinct heterotic groups.

12. A method for making a collection of seeds, wherein said method comprises:
   (a) selecting at least four target transgenes, wherein each target transgene of said at least four target transgenes comprises a regulatory region comprising an upstream activating sequence operably linked to a nucleotide sequence to be expressed, whereby said upstream activating sequence of each of said at least four target transgenes is the same or different;
   (b) selecting at least two activator transgenes, wherein each activator transgene comprises a plant promoter operably linked to a sequence encoding a chimeric polypeptide comprising a DNA binding domain fused to a transcription activation domain, wherein each DNA binding domain of said at least two chimeric polypeptides binds to the upstream activating sequence comprised within said regulatory region of at least one of said at least four target transgenes;
   (c) obtaining a first parental plant and a second parental plant, wherein each of said at least four target transgenes and said at least two activator transgenes (i) is individually present in either said first parental plant or said second parental plant, (ii) is unlinked from each of the other of said at least four target transgenes and said at least two activator transgenes that are present within the same said first parental plant or said second parental plant, and (iii) is in a hemizygous state within said first parental plant or said second parental plant;
   (d) sexually crossing said first parental plant and said second parental plant to produce a population of progeny plants, whereby said population of progeny plants has different combinations of said at least four target transgenes and said at least two activator transgenes;
   (e) comparing different plants of said population of progeny plants to one another and selecting at least one progeny plant from said population as having said desirable phenotype to obtain a selected progeny plant;
   (f) determining which target transgenes and activator transgenes are present within said selected progeny plant, thereby identifying a combination of genetic elements responsible for said desirable phenotype of a plant; and
   (g) making a collection of seeds, wherein the cells of said seeds comprise said combination of genetic elements.

13. The method of claim 12, wherein at least one of said nucleotide sequences to be expressed is a nucleotide sequence encoding a dominant negative polypeptide.

14. The method of claim 12, wherein said first parental plant comprises said at least four target transgenes, and second parental plant comprises said at least two activator transgenes.

15. The method of claim 12, wherein said chimeric polypeptide encoded by each of said at least two activator transgenes is the same.

16. The method of claim 12, wherein said upstream activating sequence of each of said at least four target transgenes is the same.

17. The method of claim 12, wherein said plant promoter of each of said at least two activator transgenes is different.

18. The method of claim 12, wherein said method further comprises, after said step (f):
   (a1) selecting at least four target transgenes, wherein each target transgene of said at least four target transgenes comprises a regulatory region comprising an upstream activating sequence operably linked to a nucleotide sequence to be expressed, whereby said upstream activating sequence of each of said at least four target transgenes is the same or different, and wherein said selected at least four target transgenes includes said target transgenes determined to be present within said selected progeny plant in step (f);
   (b1) selecting at least two activator transgenes, wherein each activator transgene comprises a plant promoter operably linked to a sequence encoding a chimeric polypeptide comprising a DNA binding domain fused to a transcription activation domain, wherein each DNA binding domain of said at least two chimeric polypeptides binds to the upstream activating sequence comprised within said regulatory region of at least one of said at least four target transgenes, and wherein said selected at least two activator transgenes includes said activator transgenes determined to be present within said selected progeny plant in step (f);
   (c1) obtaining a third parental plant and a fourth parental plant, wherein each of said at least four target transgenes of said step (a1) and said at least two activator transgenes of said step (b1) (i) is individually present in either said third parental plant or said fourth parental plant, (ii) is unlinked from each of the other of said at least four target transgenes and said at least two activator transgenes that are present within the same said third parental plant or said fourth parental plant, and (iii) is in a hemizygous state within said third parental plant or said fourth parental plant;
   (d1) sexually crossing said third parental plant and said fourth parental plant to produce a second population of progeny plants, whereby said second population of progeny plants has different combinations of said at least four target transgenes of step (a1) and said at least two activator transgenes of step (b1);
   (e1) comparing different plants of said second population of progeny plants to one another and selecting at least one progeny plant from said second population as having a desirable phenotype to obtain a second selected progeny plant; and
   (f1) determining which target transgenes and activator transgenes are present within said second selected progeny plant, thereby identifying a combination of genetic elements responsible for a desirable phenotype of a plant.

19. The method of claim 12, wherein said first parental plant and said second parental plant are selected from the group consisting of *Zea mays, Sorghum bicolor, Triticum aestivum*, and *Oryza sativa*.

20. The method of claim 12, wherein said first parental plant or said second parental plant is cytoplasmically male sterile.

21. The method of claim 12, wherein said selecting of step (e) is based at least in part on results under field testing conditions.

22. The method of claim 12, wherein said first parental plant and said second parental plant belong to distinct heterotic groups.

23. The method of claim 1, wherein said DNA binding domain is of non-plant origin.

24. The method of claim 23, wherein said DNA binding domain is a yeast or bacterial DNA binding domain.

25. The method of claim 12, wherein said DNA binding domain is of non-plant origin.

26. The method of claim 25, wherein said DNA binding domain is a yeast or bacterial DNA binding domain.

* * * * *

UNITED STATES PATENT AND TRADEMARK OFFICE
CERTIFICATE OF CORRECTION

| | | |
|---|---|---|
| PATENT NO. | : 9,101,100 B1 | Page 1 of 1 |
| APPLICATION NO. | : 14/327217 | |
| DATED | : August 11, 2015 | |
| INVENTOR(S) | : Pennell et al. | |

It is certified that error appears in the above-identified patent and that said Letters Patent is hereby corrected as shown below:

In the claims

Column 50, line 24 Claim 7, delete "trans genes" and insert -- transgenes --, therefor;

Column 50, line 40 Claim 7, after "(i)" insert -- is --, therefor;

Column 50, line 43 Claim 7, delete "trans genes" and insert -- transgenes --, therefor;

Column 50, line 43 Claim 7, delete "trans genes" and insert -- transgenes --, therefor.

Signed and Sealed this
Twenty-second Day of December, 2015

Michelle K. Lee
*Director of the United States Patent and Trademark Office*